United States Patent
Yu et al.

(10) Patent No.: US 11,555,014 B2
(45) Date of Patent: Jan. 17, 2023

(54) HIGH PENETRATION PRODRUG COMPOSITIONS OF PROSTAGLANDINS AND RELATED COMPOUNDS

(75) Inventors: Chongxi Yu, Plainfield, IL (US); Lina Xu, Shanghai (CN)

(73) Assignee: Techfields Pharma Co., Ltd., Suzhou (CN)

(*) Notice: Subject to any disclaimer, the term of this patent is extended or adjusted under 35 U.S.C. 154(b) by 0 days.

(21) Appl. No.: 12/417,621

(22) Filed: Apr. 2, 2009

(65) Prior Publication Data

US 2009/0252685 A1  Oct. 8, 2009

Related U.S. Application Data

(63) Continuation-in-part of application No. PCT/IB2006/053594, filed on Oct. 2, 2006.

(51) Int. Cl.
    *C07C 405/00* (2006.01)
(52) U.S. Cl.
    CPC .............................. *C07C 405/0041* (2013.01)
(58) Field of Classification Search
    CPC .................................................... C07C 405/00
    See application file for complete search history.

(56) References Cited

U.S. PATENT DOCUMENTS

| | | | |
|---|---|---|---|
| 3,821,279 A * | 6/1974 | Kurono et al. | C07C 405/00 546/342 |
| 3,981,868 A | 9/1976 | Bernady et al. | |
| 4,207,332 A | 6/1980 | Hayashi et al. | |
| 4,543,353 A | 9/1985 | Faustini et al. | |
| 4,699,920 A | 10/1987 | Skuballa et al. | |
| 4,746,509 A | 5/1988 | Haggiage et al. | |
| 5,164,412 A | 11/1992 | Konishi et al. | |
| 5,622,944 A | 4/1997 | Hale et al. | |
| 5,688,819 A | 11/1997 | Woodward et al. | |
| 5,756,818 A | 5/1998 | Buchmann et al. | |
| 5,885,597 A | 3/1999 | Botknecht et al. | |
| 6,011,049 A | 1/2000 | Whitcomb | |
| 6,291,528 B1 | 9/2001 | Scott | |
| 6,346,278 B1 | 2/2002 | Macrides et al. | |
| 6,416,772 B1 | 7/2002 | Van Engelen et al. | |
| 6,444,234 B1 | 9/2002 | Kirby et al. | |
| 6,528,040 B1 | 3/2003 | Pearson et al. | |
| 6,555,542 B1 | 4/2003 | O'Connor et al. | |
| 6,693,135 B2 | 2/2004 | Yeager et al. | |
| 7,052,715 B2 | 5/2006 | Fishman | |
| 7,256,210 B2 | 8/2007 | Man et al. | |
| 2004/0229920 A1 | 11/2004 | Garvey et al. | |
| 2005/0107463 A1* | 5/2005 | Woodward et al. | 514/443 |

FOREIGN PATENT DOCUMENTS

| | | |
|---|---|---|
| CA | 951314 | 7/1974 |
| EP | 0364417 | 4/1990 |
| FR | 2230620 A1 | 12/1974 |
| FR | 2235925 A1 | 1/1975 |
| GB | 1356581 | 6/1974 |
| GB | 2006754 A * | 5/1979 |
| RU | 2148351 C1 | 5/2000 |
| RU | 2150203 C1 | 6/2000 |
| RU | 2167586 C2 | 5/2001 |
| RU | 2170527 C2 | 7/2001 |
| WO | WO 93/07902 | 4/1993 |
| WO | WO 9314743 A2 * | 8/1993 |
| WO | WO 1994/005631 | 3/1994 |
| WO | 1994/08587 | 4/1994 |
| WO | WO 2003/022270 A1 | 3/2003 |
| WO | WO 2004/071428 A2 | 8/2004 |
| WO | WO 2006/083841 A2 | 8/2006 |
| WO | WO 2008/007171 A1 | 1/2008 |
| WO | WO 2008/010025 A1 | 1/2008 |
| WO | WO 2008/012602 A1 | 1/2008 |
| WO | WO 2008/012603 A1 | 1/2008 |
| WO | WO 2008/021605 A1 | 1/2008 |

(Continued)

OTHER PUBLICATIONS

J. G. Cannon "Analog Design", Chapter Nineteen in Burger's Medicinal Chemistry and Drug Discovery, Fifth Edition, vol. I: Principles and Practice, Wiley-Interscience 1995, pp. 783-802, 784.*

Ho et al. "The percutaneous penetration of prostaglandin E1 and its alkyl esters" Journal of Controlled Release, 1999, vol. 58, pp. 349-355.*

Patani et al. "Bioisosterism: A Rational Approach in Drug Design" Chem. Rev., 1996, vol. 96, pp. 3147-3176.*

Berge et al. "Pharmaceutical Salts" Journal of Pharmaceutical Sciences, 1977, vol. 66, No. 1, pp. 1-19.*

Sheridan, R. P. "The Most Common Chemical Replacements in Drug-Like Compounds" J. Chem. Inf. Comput. Sci., 2002, 42, pp. 103-108. (Year: 2002).*

(Continued)

*Primary Examiner* — Samira J Jean-Louis

(74) *Attorney, Agent, or Firm* — Fox Rothschild LLP

(57) ABSTRACT

The invention provides compositions of novel high penetration compositions (HPC) or high penetration prodrugs (HPP) of prostaglandins or prostaglandin analogs which are capable of crossing biological barriers with high penetration efficiency. The HPPs are capable of being converted to parent prostaglandins or prostaglandin analogs after crossing the biological barrier and thus can render treatments for the conditions that the parent prostaglandins or prostaglandin analogs can. Additionally, the HPPs are capable of reaching areas that parent prostaglandins or prostaglandin analogs may not be able to access or to render a sufficient concentration at the target areas and therefore render novel treatments. The HPPs can be administered to a subject through various administration routes, e.g., locally delivered to an action site of a condition with a high concentration or systematically administered to a biological subject and enter the general circulation with a faster rate.

8 Claims, 3 Drawing Sheets

(56) References Cited

FOREIGN PATENT DOCUMENTS

| | | |
|---|---|---|
| WO | WO 2008/017903 A1 | 2/2008 |
| WO | WO 2008/020270 A1 | 2/2008 |
| WO | WO 2008/026776 | 3/2008 |
| WO | WO 2008/029199 A1 | 3/2008 |
| WO | WO 2008/029200 A1 | 3/2008 |
| WO | WO 2008/044095 A1 | 4/2008 |
| WO | WO 2008/093173 A1 | 8/2008 |
| WO | WO 2008/149181 A1 | 12/2008 |

OTHER PUBLICATIONS

Bastin et al. Organic Process Research & Development (2000), vol. 4, pp. 427-435 (Year: 2000).*

Dragoli, D. R., et al., "Parallel Synthesis of Prostaglandin E1 Analogues," J. Comb. Chern. 1:534-539 (1999).

Smukste, L, et al., "Using Small Molecules to Overcome Drug Resistance Induced by a Viral Oncogene," Cancer Cell 9 (2):133-146 (2006).

Berge, S.M., et al., "Pharmaceutical Salts," J. Pharm. Sci. 66(1):1-19 (1977).

Borne, R. F., "Nonsteroidal Anti-Inflammatory Drugs," Principles of Medicinal Chemistry, 4th Ed., Williams & Wilkins, 1995, p. 535-580.

Milosovich, S., et al., "Testosteronyl-4-Dimethylaminobutyrate-HCI: A Prodrug with Improved Skin Penetration Rate," J. Pharm. Sci. 82(2):227-228 (1993).

Padma-Nathan, H., et al., "Treatment of Men with Erectile Dysfunction with Transurethral Alprostadil," N. Eng. J. Med., 336(1):1-7 (1997).

Amin, R. C., et al., "Diethylaminoethyl Dialkylacetates," J. Amer. Pharma. Association 37:243-245 (1948).

Andrews, J. M., "Determination of Minimum Inhibitory Concentrations," Journal of Antimicrobial Chemotherapy 48, suppl. S1: 5-16 (2001).

Battaglino, R., et al., "Fluoxetine Treatment Increases Trabecular Bone Formation in Mice (Fluoxetine Affects Bone Mass)," J. Cell Biochem. 100(6):1387-1394 (2007).

Drachmae, D.B., et al., "Cycloxygenase 2 Inhibition Protects Motor Neurons and Prolongs Survival in a Transgenic Mouse Model of ALS," Annals of Neurology 52:771-778 (2002).

Erlanson-Albertsson, C., et al., "Enterostatin-A Peptide Regulating Fat Intake," Obes. Res. 5(4):360-372 (1997).

Ginaldi, L., et al., "Osteoporosis, Inflammation and Ageing," Immunity & Ageing 2:14 (2005).

Hovgaard, L., et al., "Drug Delivery Studies in Caco-2 Monolayers. Synthesis, Hydrolysis, and Transport of O-Cyclopropane Carboxylic Acid Ester Prodrugs of Various B-Blocking Agents," Pharm. Res. 12(3):387-392 (1995).

Hovgaard, L., et al., "Permeation Studies on O-Cyclopropanoyl Ester Prodrugs of B-Blockers in Caco-2 Cell Monolayers," Proceed. Intern: Symp. Control. Rei. Bioact. Mater. 20:238-239 (1993).

Pan, D.S., et al., "Inhibitory Effect of Progesterone on Inflammatory Factors after Experimental Traumatic Brain Injury," Biomed. Environ. Sci. 20(5):432-438 (2007).

Raisz, L., "Pathogenesis of Osteoporosis: Concepts, Conflicts, and Prospects," J. Clin. Invest. 115(12):3318-3325 (2005).

Roof, R.L., et al., "Gender Differences in Acute CNS Trauma and Stroke: Neuroprotective Effects of Estrogen and Progesterone," J. Neurotrauma 17(5):367-388 (2000).

Scott, i. L., "Keystone Symposia: Inflammation and Cancer, Breckenridge, CO, USA, Feb. 27-Mar. 3, 2005," Technical Reports 10(13)1-17.

Sorhede, M., et al., "Enterostatin: A Gut-Brain Peptide Regulating Fat Intake in Rat," J. Physiol. 87(4):273-275 (1993).

Tozkoparan, B., et al.," 6-Benzyiidenethiazolo[3,2-b]-1,24-Triazole-5(6H)-Ones Sybstituted with Ibprofen: Synthesis, Characterization and Evaluation of Anti-Inflammatory Activity," Eur. J. Med. Chem. 35(7-8):743-750 (2000).

Wright, D.W., et al., "ProTECT: A Randomized Clinical Trial of Progesterone for Acute Traumatic Brain Injury," Ann. Emerg. Med. 49(4):391-402 (2007).

Xiao, G., et al., "Improved Outcomes from the Administration of Progesterone for Patients with Acute Severe ttraumatic bbrain iinjury: A Randomized Controlled Trial," Crit. Care 12:R61 (2008).

Yang, S., et al., "Specificity of RGS10A as a Key Component in the RANKL Signaling Mechanism for Osteoclast Differentiation," J. Cell Sci. 120:3362-3371 (2007).

Sokolov, G. P et al. "Total Synthesis and Properties of Prostaglandins. Part XXXVIII: Synthesis of 11-Deoxyprostaglandin E1 Amino Acid and Amine Derivatives," Bioorganicheskaya Khimiya, 21(5):386-390 (1995).

Jona, J. J et al. "Design of Novel Prodrugs for the Enhancement of the Transdermal Penetration of Indomethacin," International Journal of Pharmaceutics, 123(1):127-136 (1995).

Gould, P. L. "Salt Selection for Basic Drugs," International Journal of Pharmaceutics, 33: 201-217 (1986).

Korean Intellectual Property Office, International Preliminary Report on Patentability for PCT/IB2006/053594, dated Apr. 7, 2009.

Korean Intellectual Property Office, Written Opinion of the International Searching Authority for PCT/IB2006/053594, dated Jun. 20, 2007.

Johnson, M., et al., "Preparation and characterization of prostanoyl carnitine," Lipids 7(11):752-754 (1972).

\* cited by examiner

HIGH PENETRATION PRODRUG COMPOSITIONS OF PROSTAGLANDINS AND RELATED COMPOUNDS

CROSS-REFERENCE TO RELATED APPLICATIONS

The present application is a continuation-in-part application of International Application PCT/IB2006/053594, filed on Oct. 2, 2006 and published on Apr. 10, 2008 with an international publication number WO2008/041054, which is incorporated herein by reference in its entirety.

FIELD OF THE INVENTION

This invention relates to the field of pharmaceutical compositions capable of penetrating one or more biological barriers and method of using the pharmaceutical compositions for preventing, diagnosing and/or treating conditions or diseases in human and animals. The invention also relates to method of using the pharmaceutical compositions for screening new drug candidates or targets.

BACKGROUND OF THE INVENTION

Active agents or drugs that are effective in vitro may not be as effective in vivo due to delivery difficulties, in particular, their limited penetration ability across one or more biological barriers before reaching the site of action where conditions or diseases occur in vivo.

Currently, many active agents or drugs are administered through a systematic route, such as oral or parenteral administration, to reach the intended or desired site of action against a condition or disease. However, drugs delivered by systematic routes may cause adverse side reactions, e.g., caused by high dosage administration for reaching a distal location of a condition or disease.

Prostaglandins (PGs) are lipid compounds derived from fatty acids. Each prostaglandin (PG) molecule contains 20 carbon atoms, including a 5-carbon ring. Natural prostaglandins possess a 15α-hydroxy group and a trans double bond at C-13.

Prostaglandins act on a variety of cells via receptors and have a wide variety of functions, e.g., causing constriction or dilation in vascular smooth muscle cells; causing aggregation or disaggregation of platelets, sensitizing spinal neurons to pain, decreasing intraocular pressure, regulating inflammatory mediation, regulating calcium movement, controlling hormone regulation, controlling cell growth, preventing formation of the platelet plug involved in primary hemostasis (a part of blood clot formation), playing a role in cardiovascular homeostasis in relation to vascular damage, and acting as an effective vasodilator.

Prostaglandins and prostaglandin analogs have a wide variety of physiological functions and effects, and therefore have many medicinal uses. For example, prostaglandins and prostaglandin analogs can be used to induce childbirth (parturition) or abortion (e.g., $PGE_2$ or $PGF_2$, used with or without mifepristone, which is a progesterone antagonist); prevent closure of patent ductus arteriosus in newborns with particular cyanotic heart defects ($PGE_1$); prevent and treat peptic ulcers (PGE); as a vasodilator (e.g., PG analogs: iloprost and cisaprost) to treat severe Raynaud's phenomenon or ischemia of a limb or to treat pulmonary hypertension, which are treated traditionally via intravenous, subcutaneous or inhalation administration routes; treat glaucoma (e.g., in form of analogs such as bimatoprost ophthalmic solution, which is a synthetic prostamide analog with ocular hypotensive activity); and treat erectile dysfunction or in penile rehabilitation following surgery (e.g., PGE1 as alprostadil).

Unfortunately, prostaglandins and prostaglandin analogs are rapidly metabolized and inactivated by various oxidative and reductive pathways. For example, when taken orally, the drugs can be destroyed and/or inactivated in a few minutes by the first pass metabolism (i.e., the chemical breakdown of compounds in the liver and gastrointestinal tract). Additionally, if via oral or other systemic routes, the drug concentrations in the bloodstream must be sufficiently high in order to effectively reach and treat conditions or diseases in distal areas of the body. These concentrations are often much higher than the concentrations would be necessary if it were possible to accurately administer the drugs upon the particular site of condition or disease. In the case of administration by injection, the blood and liver can destroy and inactivate most of the drug compounds before they reach the intended site of action. Injection administration also has side effects, such as pain, and in many cases requires frequent and costly office visits to treat chronic conditions.

One alternative administration of drugs is topical delivery, which has several advantages, e.g., avoiding first pass metabolism and side effects as well as providing local delivery of appropriate concentrations of a drug to the intended site of action without systemic exposure.

Drug absorption requires the passage of the drug in a molecular form across one or more types of biological barriers. A drug must first dissolve, and if the drug possesses the desirable biopharmaceutical properties, it will pass from a region of high concentration to a region of low concentration across the biological barrier(s) to reach the destination, e.g., frequently via the blood or general circulation. All biological membranes contain lipids as major constituents. The molecules that play the dominant roles in membrane formation all have phosphate-containing highly polar head groups, and, in most cases, two highly hydrophobic hydrocarbon tails. Most biological membranes are bilayers, with the hydrophilic head groups facing outward into the aqueous regions on either side. Very hydrophilic drugs cannot pass the hydrophobic layer of a membrane and very hydrophobic drugs will stay in the hydrophobic layer as part of the membrane due to their similarities and cannot efficiently enter the cytosol on the inside.

Modifications of the known prostaglandins and prostaglandin analogs have been reported to improve efficiency of delivery and minimize side effects. For example, A penetration enhancer was tried to deliver $PGE_1$ for the treatment of male erectile dysfunction (U.S. Pat. No. 6,693,135 to Yeager). Milosovich et al. designed and prepared testosteronyl-4-dimethylaminobutyrate.HCl (TSBH), which has a lipophilic portion and a tertiary amine group that exists in the protonated form at physiological pH. They found that the prodrug (TSBH) diffuses through human skin about 60 times faster than does the parent drug (TS) itself (Milosovich et al., J. Pharm. Sci., 82, 227 (1993)). Fishman and many others (e.g., Van Engelen et al. U.S. Pat. No. 6,416,772; Macrides et al. U.S. Pat. No. 6,346,278; Kirby et al. U.S. Pat. No. 6,444,234, Pearson et al. U.S. Pat. No. 6,528,040 and Botknecht et al. U.S. Pat. No. 5,885,597) have attempted to develop a delivery system for transdermal application by drug formulation to reduce the side effects associating with oral administration and achieve localized drug administrations with reduced systematic exposure. However, it has been found very difficult to deliver therapeutically effective plasma levels of drugs by the formulation.

Therefore, a need exists in the art for novel compositions that are capable of being delivered efficiently and effectively to the intended site of action to prevent, reduce or treat conditions or diseases as well as minimize or avoid adverse side effects.

SUMMARY OF THE INVENTION

One aspect of the invention is directed to a high penetration prodrug (HPP) or high penetration composition (HPC) comprising a functional unit covalently linked to a transportational unit through a linker, wherein the HPP or HPC can penetrate a biological barrier more efficiently and effectively than its parent drug. The terms "HPP" and "HPC" are used alone or together herein and are interchangeable unless specifically noted.

In certain embodiments, a functional unit of a HPP or HPC comprises a moiety of an agent, wherein the efficient and effective delivery of the agent to a biological subject and/or transportation of the agent across one or more biological barriers are/is desired.

In certain embodiments, a functional unit may be hydrophilic, lipophilic, or amphiphilic (i.e., both hydrophilic and lipophilic). For example, the lipophilic nature of a function unit may be inherent or achieved by converting the hydrophilic moieties of a functional unit to lipophilic moieties.

In certain preferred embodiments, a functional unit of a HPP or HPC comprises a moiety of a prostaglandin or prostaglandin analog. A prostaglandin analog is a prostaglandin related compound which is a derivative of a prostaglandin and has similar prostaglandin related biological activities, a prostaglandin metabolite, or a compound that can be metabolized into a prostaglandin, a prostaglandin metabolite or a prostaglandin related compound after the HPP or HPC penetrates one or more biological barriers. The invention contemplates HPP or HPC of all prostaglandins and prostaglandin analogs. Examples of preferred prostaglandins and prostaglandin analogs include, but are not limited to, $PGA_1$, $PGA_2$, $PGA_3$, $PGB_1$, $PGB_2$, $PGB_3$, $PGD_1$, $PGD_2$, $PGD_3$, $PGE_1$, $PGE_2$, $PGE_3$, $PGF_{1\alpha}$, $PGF_{1\beta}$, $PGF_{2\alpha}$, $PGF_{2\beta}$, $PGF_{3\alpha}$, $PGG_2$, $PGH_1$, $PGH_2$, $PGI_2$ (prostacyclin), $PGI_3$, $PGJ_2$, $PGK_1$, $PGK_2$, carboprost, prostalene, misoprostol, gemeprost, sulprostone, fluprostenol cloprostenol, bimatoprost {(Z)-7-[(1R,2R,3R,5S)-3,5-Dihydroxy-2-[1E, 3S]-3-hydroxy-5-phenyl-1-pentenyl]cyclopentyl}-5-N-ethylheptenamide}, latanoprost (13,14-dihydro-17-phenyl-18, 19,20-trinor $PGF_{2\alpha}$ isopropyl ester), travoprost {(Z)-7-[(1R, 2R,3R,5S)-3,5-dihydroxy-2-[(1E,3R)-3-hydroxy-4-[(α,α,α-trifluoro-m-tolyl)oxy]-1-butenyl]cyclopentyl]-5-heptenoate}, and unoprostone (13,14-dihydro-15-keto-20-ethyl Prostaglandin $F_{2\alpha}$).

In certain embodiments, a transportational unit of a HPP or HPC comprises a protonatable amine group that is capable of facilitating or enhancing the transportation, penetration or crossing of the HPP or HPC through one or more biological barriers. In certain embodiments, the protonatable amine group is substantially protonated at the pH of the biological barriers through which the HPP or HPC penetrates. In certain embodiment, the amine group can be reversibly protonated or deprotonated.

In certain embodiments, a linker covalently links the functional unit to the transportational unit of a HPP and comprises a bond that is capable of being cleaved after the HPP penetrates across one or more biological barriers. The cleavable bond includes, for example, a covalent bond, an ether bond, a thioether bond, an amide bond, an ester bond, a thioester bond, a carbonate bond, a carbamate bond, a phosphate bond or an oxime bond.

Another aspect of the invention relates to a pharmaceutical composition comprising at least one HPP or HPC and a pharmaceutically acceptable carrier.

Another aspect of the invention relates to a method for diagnosing the onset, development, or remission of a condition in a biological subject by using a HPP or HPC of the invention. In certain embodiments, the HPP (or HPC) or the functional unit thereof is detectable. In certain embodiments, the HPP or the functional unit of the HPP is inherently detectable, labeled with, or conjugated to, a detectable marker.

Another aspect of the invention relates to a method for screening functional units, linkers, or transportational units of a HPP for desired characteristics.

Another aspect of the invention relates to a method for preventing, ameliorating, reducing, or treating a condition or disease in a biological subject by administering to the subject at least one HPP or a pharmaceutical composition in accordance with the invention. In certain embodiments, the method relates to the treatment of a condition or disease in a subject treatable by prostaglandins or prostaglandin analogs by administering to the subject a therapeutically effective amount of a HPP or a pharmaceutical composition of prostaglandins or prostaglandin analogs. In certain embodiment, the HPP or pharmaceutical composition of the invention can be administered to a biological subject via various routes including, but not limited to, oral, enteral, buccal, nasal, topical, rectal, vaginal, aerosol, transmucosal, epidermal, transdermal, dermal, ophthalmic, pulmonary, subcutaneous, and/or parenteral routes. In certain preferred embodiments, the HPP or pharmaceutical composition of the invention is administered orally, transdermally, topically, subcutaneously and/or parenterally.

In accordance with the advantages of the invention, without intending to be limited by any particular mechanism, a therapeutically effective amount of a HPP or pharmaceutical composition containing at least one HPP can be administered locally to a site of condition with a less dosage at a higher concentration. The advantages of the invention also include, for example, avoidance of systematic administration and reduction of adverse effects (e.g., pain of injection, gastrointestinal/renal effects, and other side effect), possible novel treatments due to high local concentration of a HPP, HPC or active agent. The advantages further include, for example, systematic administration of a HPP or HPC to a biological subject to achieve faster and more efficient bioavailability, penetration of biological barriers (e.g., the blood brain barrier) which have been difficult to cross, and new indications as a result of passing through biological barriers.

DETAILED DESCRIPTION OF THE INVENTION

Figure 1:
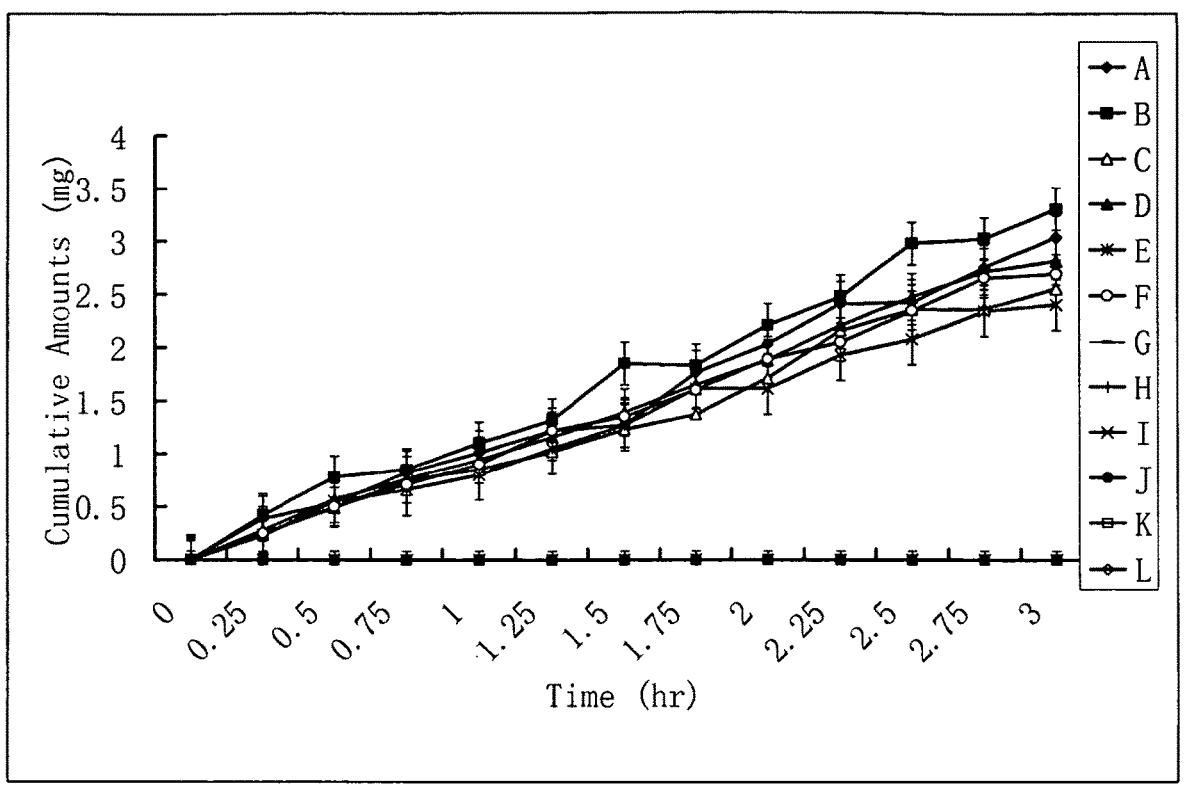
FIG. 1 depicts cumulative amounts of N,N-diethylaminoethyl 11,15-dihydroxy-9-oxoprost-13-en-1-oate.AcOH (A, 10% solution), N,N-diethylaminoethyl 11,15-dihydroxyl-9-oxoprosta-5,13-dien-1-oate.AcOH (B, 10% solution), N,N-diethylaminoethyl 9,11,15-trihydroxyprost-13-en-1-oate.AcOH(C, 10% solution), N,N-diethylaminoethyl 9,11,15-trihydroxyprosta-5,13-dien-1-oate.AcOH (D, 10% solution), N,N-diethylaminoethyl 9,11,15-trihydroxy-15-methylprosta-5,13-dien-1-oate.AcOH (E, 10% solution), N,N-diethylaminoethyl 9,11,15-trihydroxy-15-methylprosta-4,5,13-trien-1-oate.AcOH, (F, 10% solution), $PGE_1$ (G, 10% suspension), $PGE_2$ (H, 10% suspension), $PGF_1\alpha$ (I, 10% suspension), PGF$_2\alpha$ (J, 10% suspension), carboprost (K, 10% suspension), prostalene (L, 10% suspension), crossing isolated human skin tissue in Franz cells (n=5). In each case, the vehicle was pH 7.4 phosphate buffer (0.2 M).

I. Structures of High Penetration Prodrug (HPP) or High Penetration Composition (HPC)

One aspect of the invention is directed to a high penetration prodrug (HPP) or a high penetration composition (HPC) of a parent drug. The term "high penetration prodrug" ("HPP") or "high penetration composition" ("HPC") as used herein refers to a composition comprising a functional unit covalently linked to a transportational unit through a linker.

The functional unit of a HPP which comprises a moiety of a parent drug has the properties of 1) the delivery of the parent drug into a biological subject and/or transportation of the parent drug across a biological barrier are/is desired; 2) the HPP is capable of penetrating or crossing a biological barrier; and 3) the HPP is capable of being cleaved after the penetration so that the moiety of a parent drug is metabolized into the parent drug after the cleavage. In certain embodiments, the moiety of a parent drug in a functional unit is an inactive or substantially less active form of the parent drug.

In certain embodiments, a functional unit may be hydrophilic, lipophilic, or amphiphilic (hydrophilic and lipophilic). The lipophilic moiety of a function unit may be inherent or achieved by converting its hydrophilic moieties to lipophilic moieties. For example, the lipophilic moiety of a functional unit may be produced by converting one or more hydrophilic groups of the functional unit to lipophilic groups via traditional organic synthesis. Examples of the hydrophilic groups include, without limitation, carboxylic, hydroxyl, thiol, amine, phosphate/phosphonate and carbonyl groups. The lipophilic moieties produced via the modification of these hydrophilic groups include, without limitation, ethers, thioethers, esters, thioesters, carbonates, carbamates, amides, phosphates and oximes.

In certain embodiments, a parent drug of a HPP or HPC is a prostaglandin or a prostaglandin analog. The moiety of a prostaglandin or prostaglandin analog can be further converted to lipophilic moiety as described supra.

As used herein, a prostaglandin or "a prostaglandin analog" is a compound comprising a five-member ring and a fatty acid group, wherein the five-member ring may be part of a multiple ring structure. Examples of prostaglandins and prostaglandin analogs include, but are not limited to, PGA$_1$, PGA$_2$, PGA$_3$, PGB$_1$, PGB$_2$, PGB$_3$, PGD$_1$, PGD$_2$, PGD$_3$, PGE$_1$, PGE$_2$, PGE$_3$, PGF$_{1\alpha}$, PGF$_{1\beta}$, PGF$_{2\alpha}$, PGF$_{2\beta}$, PGF$_{3\alpha}$, PGG$_2$, PGH$_1$, PGH$_2$, PGI$_2$ (prostacyclin), PGI$_3$, PGJ$_2$, PGK$_1$, PGK$_2$, carboprost, prostalene, misoprostol, gemeprost, sulprostone, fluprostenol, cloprostenol, bimatoprost {(Z)-7-[(1R,2R,3R,5S)-3,5-Dihydroxy-2-[1E,3S]-3-hydroxy-5-phenyl-1-pentenyl]cyclopentyl}-5-N-ethylheptenamide}, latanoprost (13,14-dihydro-17-phenyl-18,19,20-trinor PGF$_{2\alpha}$ isopropyl ester), travoprost {(Z)-7-[(1R,2R,3R,5S)-3,5-dihydroxy-2-[(1E,3R)-3-hydroxy-4-[(α,α,α-trifluoro-m-tolyl)oxy]-1-butenyl]cyclopentyl]-5-heptenoate}, and unoprostone (13,14-dihydro-15-keto-20-ethyl PGF$_{2\alpha}$). Exemplary structures of prostaglandins and prostaglandins analogs are shown in Scheme A:

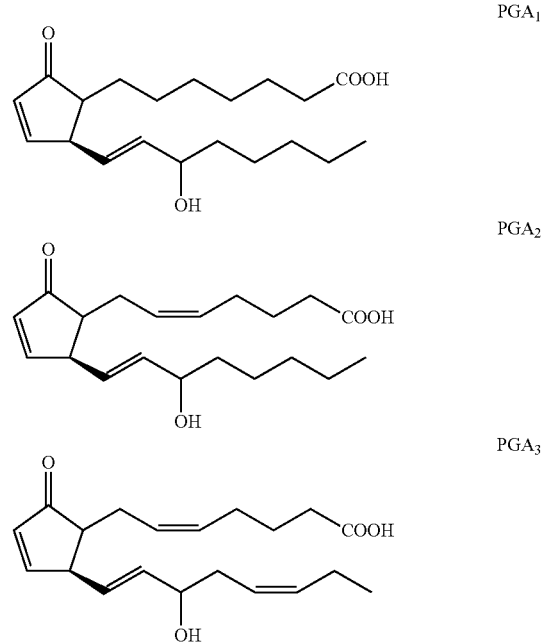

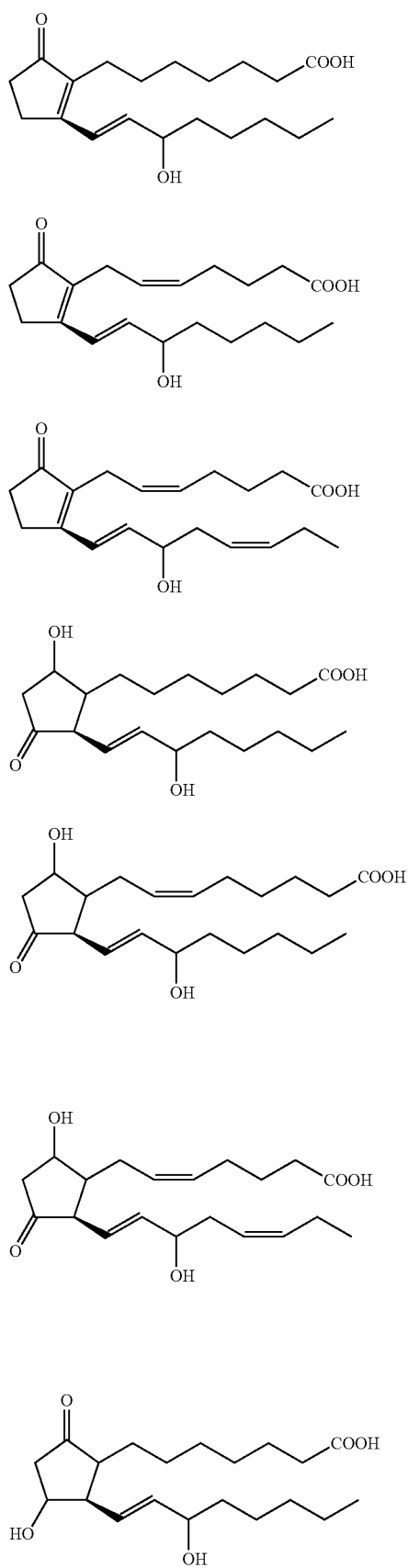
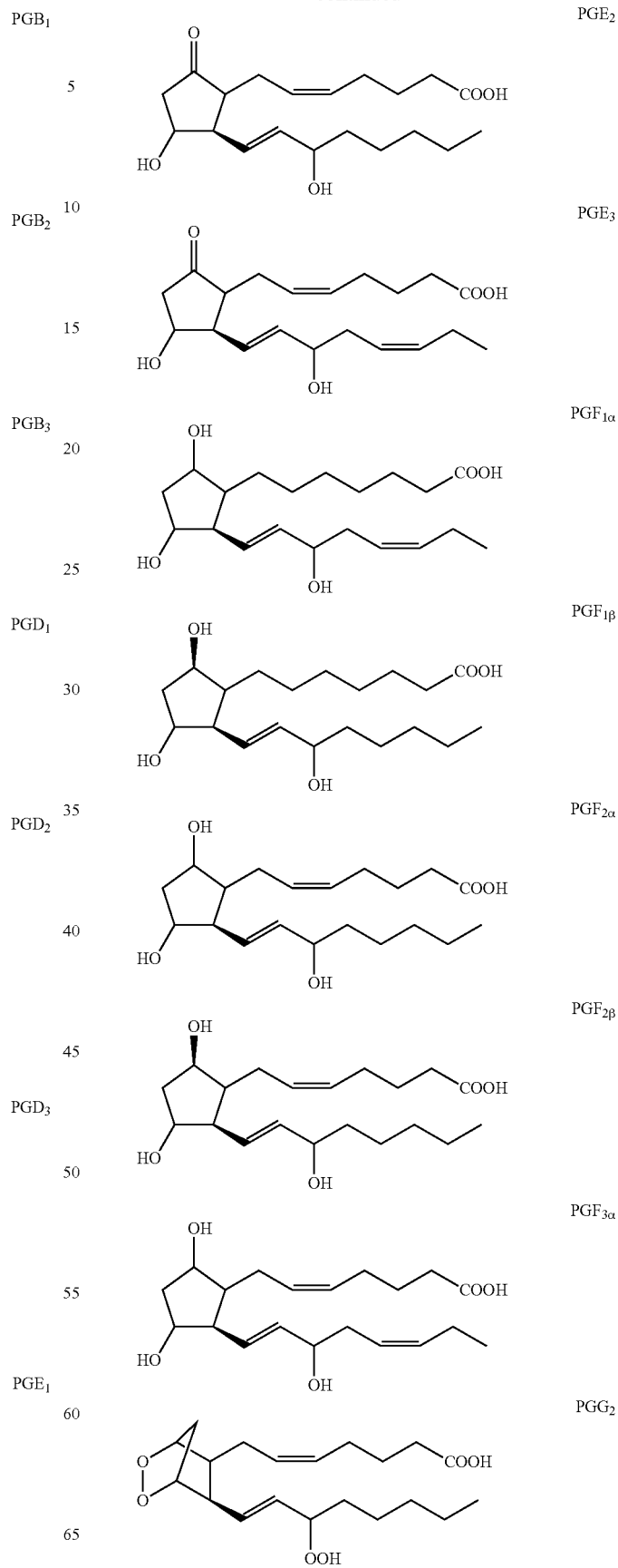

PGH₁
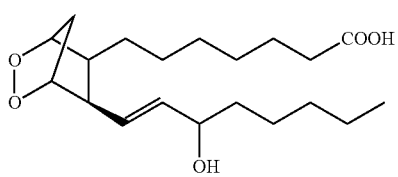

PGH₂
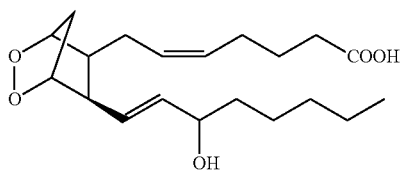

PGI₂
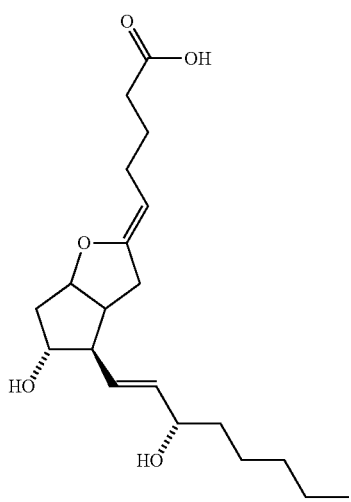

PGI₃
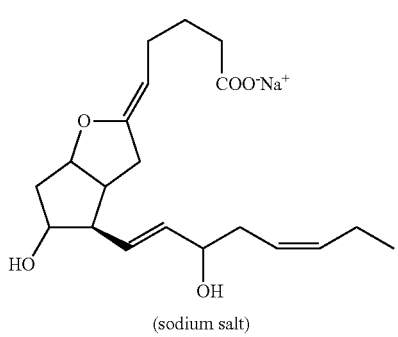
(sodium salt)

PGJ₂
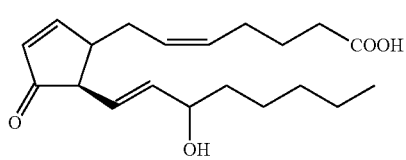

PGK₁
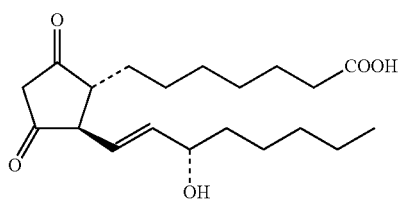

PGK₂
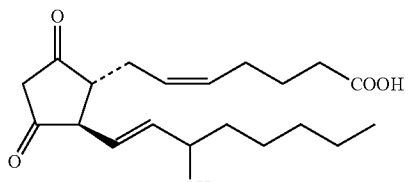

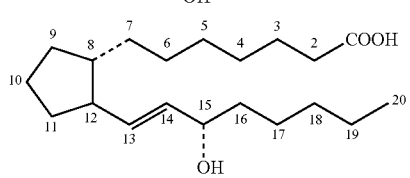
an example of PG analog

In one embodiment, a functional unit of a HPP of prostaglandins and prostaglandin analogs comprises a moiety having Structure 1:

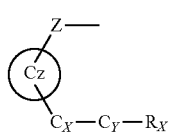

Structure 1 including stereoisomers and pharmaceutically acceptable salts thereof, wherein:

Z is selected from the group consisting of substituted and unsubstituted alkyl, substituted and unsubstituted cycloalkyl, substituted and unsubstituted heterocycloalkyl, substituted and unsubstituted aryl, substituted and unsubstituted alkoxyl, substituted and unsubstituted alkylthio, —$R_4$—CO—$R_5$—, —$(CH_2)_6$—, —$(CH_2)_m$—O—$CH_2$—, —$(CH_2)_m$—S—$CH_2$—, —$CH_2C\equiv C-(CH_2)_n$—, —$CH_2C\equiv C-(CH_2)_n$—O—$CH_2$—, —$CH_2C\equiv C-(CH_2)_n$—S—$CH_2$—, —$CH_2$—CO—$(CH_2)_n$—, —$CH_2$—CH=C=CH—$(CH_2)_n$—, —$CH_2$—CH=C=CH—O—$(CH_2)_n$—, —$CH_2$—CH=C=CH—S—$(CH_2)_n$—, Structure Za, Structure Zb, Structure Zc, Structure Zd, Structure Ze, Structure Zf, Structure Zg, Structure Zh, and Structure Zi:

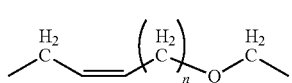
Structure Za

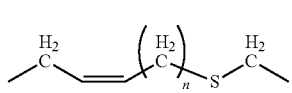
Structure Zb

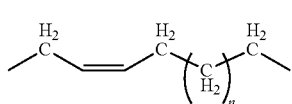
Structure Zc

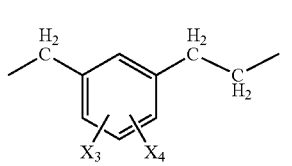
Structure Zd

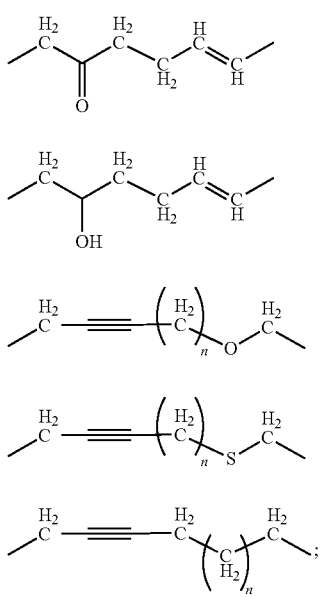

Sturcture Ze

Sturcture Zf

Sturcture Zg

Sturcture Zh

Sturcture Zi

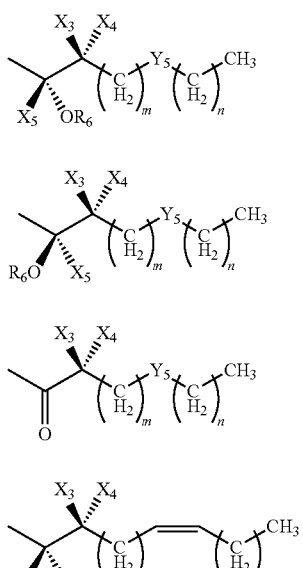

$R_x$ is selected from the group consisting of Structure $R_x$-a, Structure $R_x$-b, Structure $R_x$-c, Structure $R_x$-d, Structure $R_x$-e, Structure $R_x$-f, Structure $R_x$-g, Structure $R_x$-h, Structure $R_x$-i, Structure $R_x$-j, Structure $R_x$-k, Structure $R_x$-l, Structure $R_x$-m, Structure $R_x$-n, Structure $R_x$-o, Structure $R_x$-p, Structure $R_x$-q, and Structure $R_x$-r:

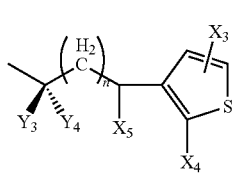

Structure $R_x$-a

Structure $R_x$-b

Structure $R_x$-c

Structure $R_x$-d

Structure $R_x$-e

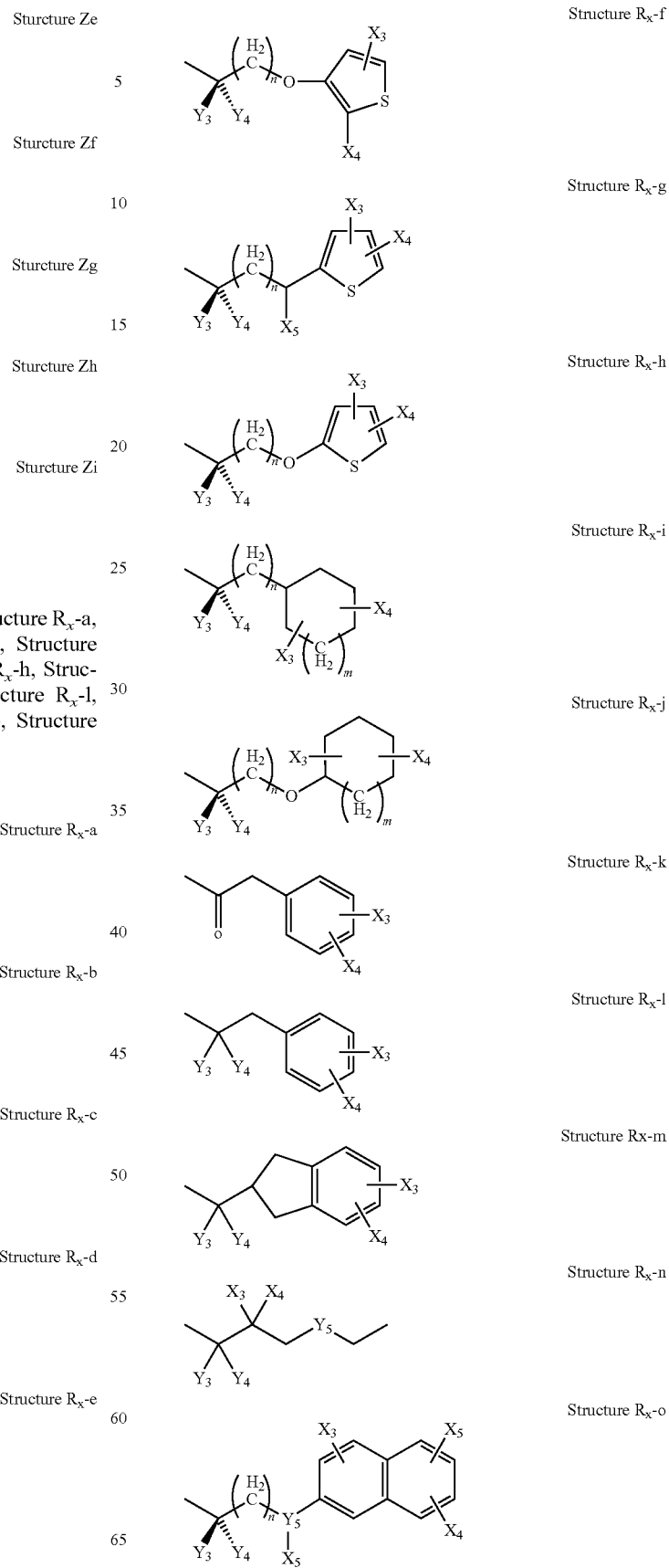

Structure $R_x$-f

Structure $R_x$-g

Structure $R_x$-h

Structure $R_x$-i

Structure $R_x$-j

Structure $R_x$-k

Structure $R_x$-l

Structure Rx-m

Structure $R_x$-n

Structure $R_x$-o

-continued

Structure R$_x$-p

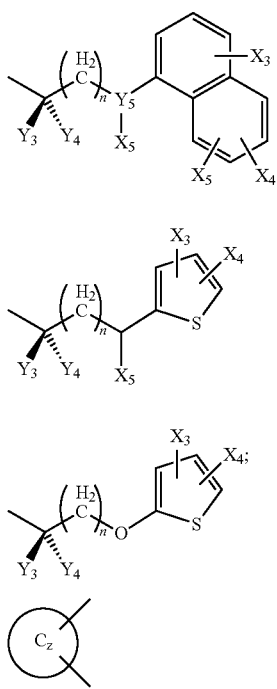

Structure R$_x$-q

Structure R$_x$-r is selected from the group consisting of Structure C$_z$-a, Structure C$_z$-b, Structure C$_z$-c, Structure C$_z$-d, Structure C$_z$-e, Structure C$_z$-f, Structure C$_z$-g, Structure C$_z$-h, Structure C$_z$-I, Structure C$_z$-j, Structure C$_z$-k, Structure C$_z$-l, Structure C$_z$-m, Structure C$_z$-n, Structure C$_z$-o, Structure C$_z$-p, and Structure C$_z$-q:

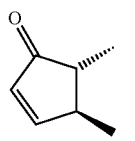

Structure C$_z$-a

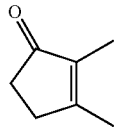

Structure C$_z$-b

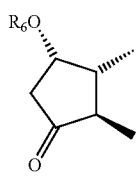

Structure C$_z$-c

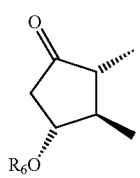

Structure C$_z$-d

-continued

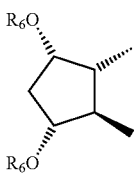

Structure C$_z$-e

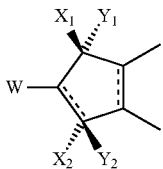

Structure C$_z$-f

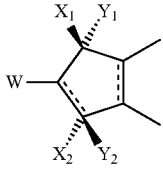

Structure C$_z$-g

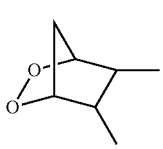

Structure C$_z$-h

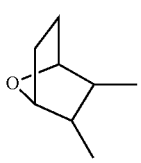

Structure C$_z$-i

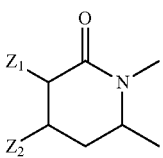

Structure C$_z$-j

Structure Cz-k

Structure C$_z$-l

Structure C$_z$-m

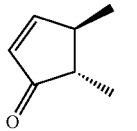

Structure C$_z$-n

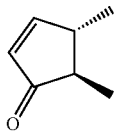

Structure C_z-o

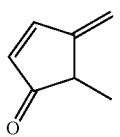

Structure C_z-p

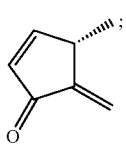

Structure C_z-q $X_3$-$X_5$ are independently selected from the group consisting of $R_4SO_2$, $R_4CO—$, $R_4S—$, H, OH, $OR_4$, Cl, F, Br, I, CN, $NO_2$, $CH_3SO_2$, $C_2H_5SO_2$, $C_3H_7SO_2$, $C_4H_9SO_2$, $CH_3CO$, $C_2H_5CO$, $C_3H_7CO$, $C_4H_9CO$, $CH_3O$, $C_2H_5O$, $C_3H_7O$, $C_4H_9O$, $CH_3S$, $C_2H_5S$, $C_3H_7S$, $C_4H_9S$, $CH_3$, $C_2H_5$, $C_3H_7$, $C_4H_9$, —CH=$CH_2$, —$CH_2$CH=$CH_2$, $CH_2CR_5$=$CR_4$, —$CR_5$=$CR_4$, CF3, $C_2F_5$, $C_3F_7$, $C_4F_9$, substituted and unsubstituted alkyl, substituted and unsubstituted alkoxyl, substituted and unsubstituted alkylthio, substituted and unsubstituted perfluoroalkyl, and substituted and unsubstituted alkyl halide;

m and n are independently selected from the group consisting of integers, 0, 1, 2, 3, 4, 5, 6, 7, 8, 9, 10, 11, 12, 13, 14, 15, 16, 17, 18, 19, 20, . . . and 100;

—$C_x$—$C_y$— is selected from the group consisting of substituted and unsubstituted alkyl, substituted and unsubstituted alkylthio, substituted and unsubstituted alkoxyl, —$CH_2$—$CH_2$—, —$CHR_4$—$CHR_5$—, —S—$CH_2$—, —S—$CHR_4$—, —O—$CH_2$—, —O—$CHR_4$—, —C≡C—, —$CR_5$=$CR_4$—, and —CH=CH—;

$R_4$ and $R_5$ are independently selected from the group consisting of H, substituted and unsubstituted alkyl, substituted and unsubstituted alkoxyl, substituted and unsubstituted perfluoroalkyl, substituted and unsubstituted alkyl halide, substituted and unsubstituted aryl, substituted and unsubstituted $C_1$-$C_{20}$ alkyl, substituted and unsubstituted $C_1$-$C_{20}$ alkoxyl, substituted and unsubstituted $C_1$-$C_{20}$ perfluoroalkyl, substituted and unsubstituted $C_1$-$C_{20}$ alkyl halide, and substituted and unsubstituted $C_1$-$C_{20}$ aryl, wherein any $CH_2$ may be replaced with O, S, $NR_4$, or other groups $Y_1$-$Y_4$ and $X_1$-$X_2$ are the same or different and each is substituted or unsubstituted alkyl, substituted or unsubstituted alkoxyl, —$R_4OCOR_5$, —$OCOR_5$, $R_5$, —$R_5$—OH, H, OH, $OR_5$, OOH, $OCOCH_3$, $OCOC_2H_5$, $OCOC_3H_7$, $OCOC_4H_9$, $OCOC_5H_{11}$, $OCOC_6H_{13}$, $CH_3$, $CH_2OH$, $CH_2OCOCH_3$, $CH_2OCOC_2H_5$, $CH_2OCOC_3H_7$, $CH_2OCOC_4H_9$, Cl, F, Br, or I, or $Y_3$ and $Y_4$ taken together is =O, $Y_1$ and $X_1$ taken together is =O, or $Y_2$ and $X_2$ taken together is =O;

$Y_5$ is selected from the group consisting of $C(R_4)(R_5)$, $N(R_4)$, $CH_2$, CH, N, NH, S, and O;

$R_6$ is selected from the group consisting of —$COR_4$, H, OH, acetyl, propionyl, isobutyryl, butyryl, pivaloyl, valeryl, and isovaleryl;

$Z_1$ and $Z_2$ are independently selected from the group consisting of $OCOR_5$, $R_4OCOR_5$, $R_5OH$, $R_5$, H, OH, $OR_5$, OOH, $OCOCH_3$, $OCOC_2H_5$, $OCOC_3H_7$, $OCOC_4H_9$, $OCOC_5H_{11}$, $OCOC_6H_{13}$, $CH_3$, $CH_2OH$, $CH_2OCOCH_3$, $CH_2OCOC_2H_5$, $CH_2OCOC_3H_7$, $CH_2OCOC_4H_9$, Cl, F, Br, and I; and the dashed bonds represent a single or double bond.

As used herein, the term "pharmaceutically acceptable salt" means those salts of compounds of the invention that are safe and effective for application in a subject and that possess the desired biological activity. Pharmaceutically acceptable salts include salts of acidic or basic groups present in compounds of the invention. Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,11-methylene-bis-(2-hydroxy-3-naphthoate)) salts. Certain compounds of the invention can form pharmaceutically acceptable salts with various amino acids. Suitable base salts include, but are not limited to, aluminum, calcium, lithium, magnesium, potassium, sodium, zinc, and diethanolamine salts. For a review on pharmaceutically acceptable salts see BERGE ET AL., 66 J. PHARM. SCI. 1-19 (1977), incorporated herein by reference.

As used herein, unless specified otherwise, the term "alkyl" means a branched or unbranched, saturated or unsaturated, monovalent or multivalent hydrocarbon group. Examples of alkyl include, but are not limited to, methyl, ethyl, propyl, isopropyl, butyl, isobutyl, t-butyl, pentyl, hexyl, heptyl, octyl, nonyl, decyl, undecyl, dodecyl, ethenyl, propenyl, butenyl, isobutenyl, pentenyl, hexenyl, heptenyl, octenyl, nonenyl, decenyl, undecenyl, dodecenyl, ethynyl, propynyl, butynyl, isobutynyl, pentynyl, hexynyl, heptynyl, octynyl, nonynyl, decynyl, undecynyl, dodecynyl, methylene, ethylene, propylene, isopropylene, butylene, isobutylene, t-butylene, pentylene, hexylene, heptylene, octylene, nonylene, decylene, undecylene and dodecylene, In certain embodiments, the hydrocarbon group contains 1 to 30 carbons. In certain embodiments, the hydrocarbon group contains 1 to 20 carbons As used herein, unless specified otherwise, the term "cycloalkyl" means an alkyl which contains at least one ring and no aromatic rings. Examples of cycloalkyl include, but are not limited to, cyclopropyl, cyclobutyl, cyclopentyl, cyclohexyl, cycloheptyl, cyclooctyl, cyclononyl, cyclodecyl, cycloundecyl and cyclododecyl. In certain embodiments, the hydrocarbon chain contains 1 to 30 carbons. In certain embodiments, the hydrocarbon group contains 1 to 20 carbons.

As used herein, unless specified otherwise, the term "heterocycloalkyl" means a cycloalkyl wherein at least one ring atom is a non-carbon atom. Examples of the non-carbon ring atom include, but are not limited to, S, O and N.

As used herein, unless specified otherwise, the term "alkoxyl" means an alkyl, cycloalkyl or heterocycloalkyl, which contains one or more oxygen atoms. Examples of alkoxyl include, but are not limited to, —$CH_2$—OH, —$OCH_3$, —O-alkyl, -alkyl-OH, -alkyl-O-alkyl-, wherein the two alkyls can be the same or different.

As used herein, unless specified otherwise, the term "alkyl halide" means an alkyl, cycloalkyl or heterocycloalkyl, which contains one or more halogen atoms, wherein the halogen atoms can be the same or different. The term "halogen" means fluorine, chlorine, bromine or iodine. Examples of alkyl halide include, but are not limited to, -alkyl-F, -alkyl-Cl, -alkyl-Br, -alkyl-I, -alkyl(F)—, -alkyl(Cl)—, -alkyl(Br)— and -alkyl(I)—.

As used herein, unless specified otherwise, the term "alkylthio" means an alkyl, cycloalkyl or heterocycloalkyl, which contains one or more sulfur atoms. Examples of alkylthio include, but are not limited to, —CH$_2$—SH, —SCH$_3$, —S-alkyl, -alkyl-SH, -alkyl-S-alkyl-, wherein the two alkyls can be the same or different.

As used herein, unless specified otherwise, the term "perfluoroalkyl" means an alkyl, cycloalkyl or heterocycloalkyl, which contains one or more fluoro group, including, without limitation, perfluoromethyl, perfluoroethyl, perfluoropropyl.

As used herein, unless specified otherwise, the term "aryl" means a chemical structure comprising one or more aromatic rings. In certain embodiments, the ring atoms are all carbon. In certain embodiments, one or more ring atoms are non-carbon, e.g. oxygen, nitrogen, or sulfur. Examples of aryl include, without limitation, phenyl, benzyl, naphthalenyl, anthracenyl, pyridyl, quinoyl, isoquinoyl, pyrazinyl, quinoxalinyl, acridinyl, pyrimidinyl, quinazolinyl, pyridazinyl, cinnolinyl, imidazolyl, benzimidazolyl, purinyl, indolyl, furanyl, benzofuranyl, isobenzofuranyl, pyrrolyl, indolyl, isoindolyl, thiophenyl, benzothiophenyl, pyrazolyl, indazolyl, oxazolyl, benzoxazolyl, isoxazolyl, benzisoxazolyl, thiaxolyl and benzothiazolyl.

In certain embodiments, a transportational unit of the HPP comprises a protonatable amine group that is capable of facilitating the transportation or crossing of the HPP through one or more biological barriers (approximately >10 times, approximately >50 times, approximately >100 times, approximately >300 times, approximately >500 times, approximately >1,000 times, or approximately >10,000 times faster than the agent or parent drug). In certain embodiments, the protonatable amine group is substantially protonated at the physiological pH of the biological barrier. In certain embodiment, the amine group can be reversibly protonated. In certain embodiment, the transportational unit may or may not be cleaved from the functional unit after the penetration of HPP through one or more biological barriers.

In certain embodiments, the protonatable amine group is selected from the group consisting of pharmaceutically acceptable substituted and unsubstituted primary amine groups, pharmaceutically acceptable substituted and unsubstituted secondary amine groups, and pharmaceutically acceptable substituted and unsubstituted tertiary amine groups.

In certain embodiments, the protonatable amine group is selected from the group consisting of Structure Na, Structure Nb, Structure Nc, Structure Nd, Structure Ne, Structure Nf, Structure Ng, Structure Nh, Structure Ni, Structure Nj, Structure Nk, Structure Nl, Structure Nm, Structure Nn, Structure No, Structure Np, Structure Nq and Structure Nr:

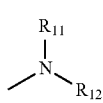

Structure Na

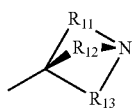

Structure Nb

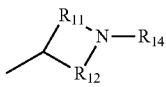

Structure Nc

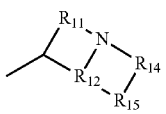

Structure Nd

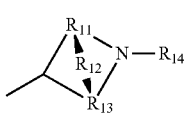

Structure Ne

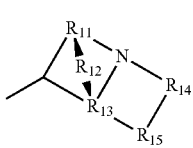

Structure Nf

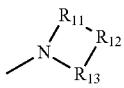

Structure Ng

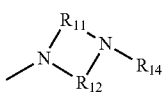

Structure Nh

Structure Ni

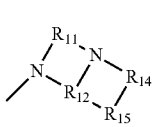

Structure Nj

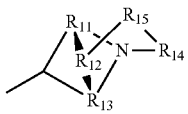

Structure Nk

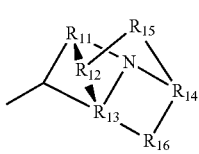

Structure Nl

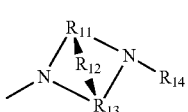

Structure Nm

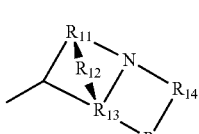

Structure Nn

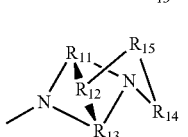

Structure No

-continued

Structure Np

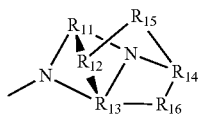

Structure Nq

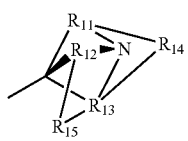

Structure Nr

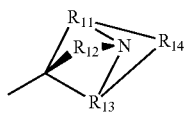

including stereoisomers and pharmaceutically acceptable salts thereof.

As used herein, unless specified otherwise, each $R_{11}$-$R_{16}$ is independently selected from the group consisting of nothing, H, $CH_2COOR_{11}$, substituted and unsubstituted alkyl, substituted and unsubstituted cycloalkyl, substituted and unsubstituted heterocycloalkyl, substituted and unsubstituted aryl, substituted and unsubstituted alkoxyl, substituted and unsubstituted alkylthio, substituted and unsubstituted alkylamino, substituted and unsubstituted perfluoroalkyl, and substituted and unsubstituted alkyl halide, wherein any carbon or hydrogen may be further independently replaced with O, S, P, $NR_{11}$, or any other pharmaceutically acceptable groups.

In certain embodiments, the linker covalently linking a functional unit to a transportational unit comprises a bond that is capable of being cleaved after the HPP penetrates across one or more biological barriers. The cleavable bond comprises, for example, a covalent bond, an ether, thioether, amide, ester, thioester, carbonate, carbamate, phosphate or oxime bond.

In certain embodiments, a HPP or HPC of the invention comprises the following Structure L:

Structure L

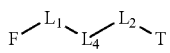

including stereoisomers and pharmaceutically acceptable salts thereof, wherein:

F is a functional unit of a HPP of prostaglandin or prostaglandin analog. Examples of F include Structure 1 as defined supra;

T is a transportational unit of a HPP of prostaglandin or prostaglandin analog. For example, T is selected from the group consisting of Structure Na, Structure Nb, Structure Nc, Structure Nd, Structure Ne, Structure Nf, Structure Ng, Structure Nh, Structure Ni, Structure Nj, Structure Nk, Structure Nl, Structure Nm, Structure Nn, Structure No, Structure Np, Structure Nq and Structure Nr as defined supra;

$L_1$ is selected from the group consisting of nothing, O, S, —N($L_3$)-, —N($L_3$)-$CH_2$—O, —N($L_3$)-$CH_2$—N($L_5$)-, —O—$CH_2$—O—, —O—CH($L_3$)-O, and —S—CH($L_3$)-O—;

$L_2$ is selected from the group consisting of nothing, O, S, —N($L_3$)-, —N($L_3$)-$CH_2$—O, —N($L_3$)-$CH_2$—N($L_5$)-, —O—$CH_2$—O—, —O—CH($L_3$)-O, —S—CH($L_3$)-O—, —O-$L_3$-, —N-$L_3$-, —S-$L_3$-, —N($L_3$)-$L_5$- and $L_3$;

$L_4$ is selected from the group consisting of C=O, C=S,

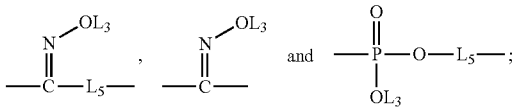

each $L_3$ and $L_5$ is independently selected from the group consisting of nothing, H, $CH_2COOL_6$, substituted and unsubstituted alkyl, substituted and unsubstituted cycloalkyl, substituted and unsubstituted heterocycloalkyl, substituted and unsubstituted aryl, substituted and unsubstituted alkoxyl, substituted and unsubstituted alkylthio, substituted and unsubstituted alkylamino, substituted and unsubstituted perfluoroalkyl, and substituted and unsubstituted alkyl halide, wherein any carbon or hydrogen may be further independently replaced with O, S, P, $NL_3$, or any other pharmaceutically acceptable groups;

$L_6$ is selected from the group consisting of H, OH, Cl, F, Br, I, substituted and unsubstituted alkyl, substituted and unsubstituted cycloalkyl, substituted and unsubstituted heterocycloalkyl, substituted and unsubstituted aryl, substituted and unsubstituted heteroaryl, substituted and unsubstituted alkoxyl, substituted and unsubstituted alkylthio, substituted and unsubstituted alkylamino, substituted and unsubstituted perfluoroalkyl, and substituted and unsubstituted alkyl halide, wherein any carbon or hydrogen may be further independently replaced with O, S, N, P(O)$OL_6$, CH=CH, C≡C, $CHL_6$, $CL_6L_7$, aryl, heteroaryl, or cyclic groups; and $L_7$ is selected from the group consisting of H, OH, Cl, F, Br, I, substituted and unsubstituted alkyl, substituted and unsubstituted cycloalkyl, substituted and unsubstituted heterocycloalkyl, substituted and unsubstituted aryl, substituted and unsubstituted heteroaryl, substituted and unsubstituted alkoxyl, substituted and unsubstituted alkylthio, substituted and unsubstituted alkylamino, substituted and unsubstituted perfluoroalkyl, and substituted and unsubstituted alkyl halide, wherein any carbon or hydrogen may be further independently replaced with O, S, N, P(O)$OL_6$, CH=CH, C≡C, $CHL_6$, $CL_6L_7$, aryl, heteroaryl, or cyclic groups.

In certain embodiments, a HPP or HPC of the invention comprises the structure of Structure L, including stereoisomers and pharmaceutically acceptable salts thereof, wherein F, $L_1$, $L_2$ and T are defined as supra and $L_4$ is C=O.

I-1. Examples of HPP of Prostaglandins and Prostaglandin Analogs.

In certain embodiments, a HPP of prostaglandins and prostaglandin analogs includes a compound having the formula of Structure 2, including stereoisomers and pharmaceutically acceptable salts thereof.

Structure 2 is selected from the group consisting of Structure 2a, Structure 2b, Structure 2c, Structure 2d, Structure 2e, Structure 2f, Structure 2g, Structure 2h, Structure 2i, Structure 2j, Structure 2k, Structure 2l, Structure 2m, Structure 2n, Structure 2o, Structure 2p, Structure 2q, and Structure 2r:

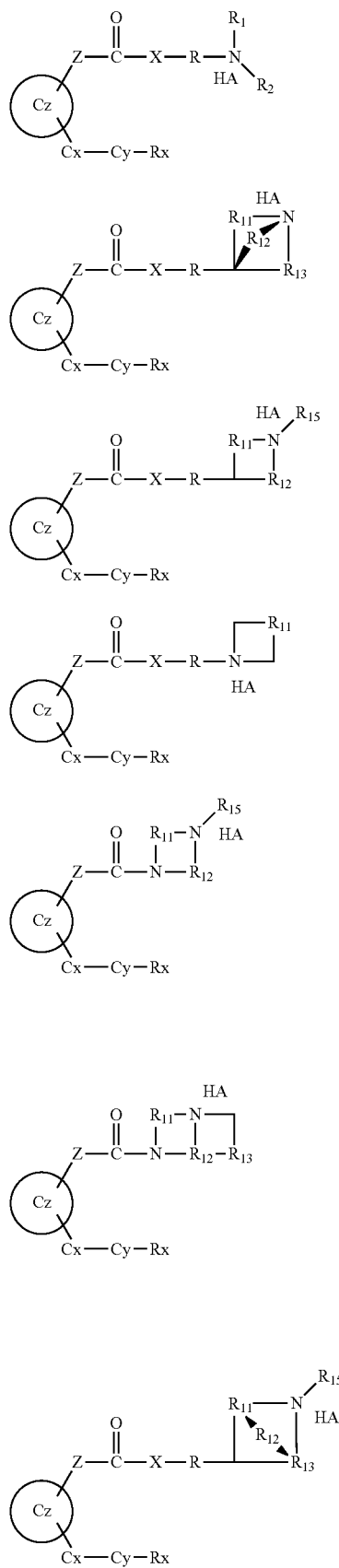
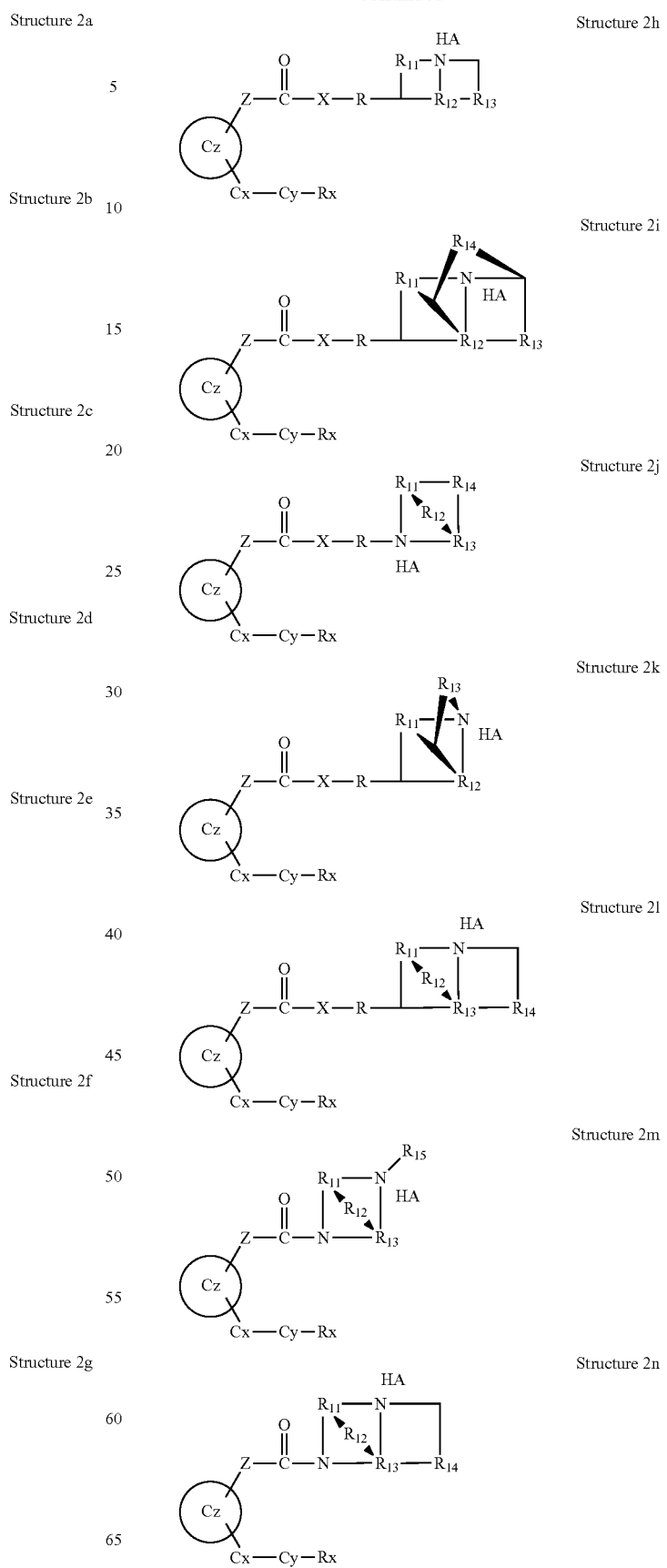

-continued

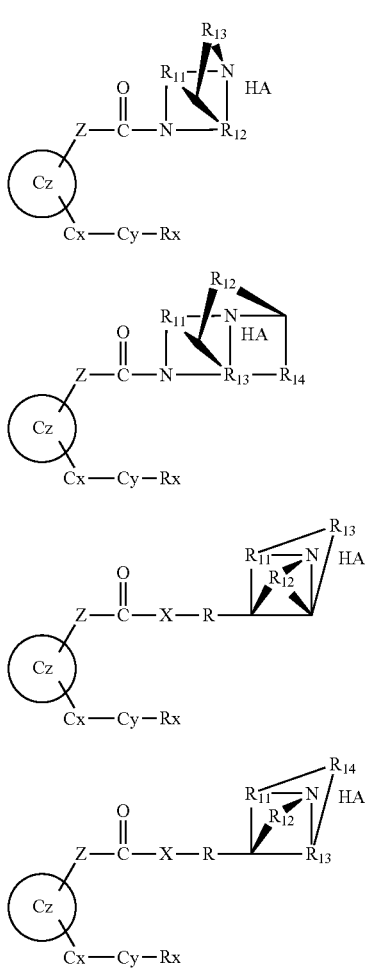

Structure 2o

Structure 2p

Structure 2q

Structure 2r including stereoisomers and pharmaceutically acceptable salts thereof, wherein:

R is selected from the group consisting of substituted and unsubstituted 0-20 carbon atoms alkyl, substituted and unsubstituted 1-20 carbon atoms alkoxyl, substituted and unsubstituted 1-20 carbon atoms perfluoroalkyl, substituted and unsubstituted 1-20 carbon atoms alkyl halide, substituted and unsubstituted 2-20 carbon atoms alkenyl, substituted and unsubstituted 2-20 carbon atoms alkynyl, substituted and unsubstituted 6-20 carbon atoms aryl, and substituted and unsubstituted 2-20 carbon atoms heteroaryl moieties which are pharmaceutically acceptable, wherein any $CH_2$ may be replaced with O, S, $NR_{11}$, or other groups;

$R_1$, $R_2$, and $R_{11}$-$R_{15}$ are independently selected from the group consisting of H, substituted and unsubstituted 1-20 carbon atoms alkyl, substituted and unsubstituted 1-20 carbon atoms alkoxyl, substituted and unsubstituted 1-20 carbon atoms perfluoroalkyl, substituted and unsubstituted 1-20 carbon atoms alkyl halide, substituted and unsubstituted 2-20 carbon atoms alkenyl, substituted and unsubstituted 2-20 carbon atoms alkynyl, substituted and unsubstituted 3-20 carbon atoms aryl, and substituted and unsubstituted 2-20 carbon atoms heteroaryl moieties which are pharmaceutically acceptable, wherein any $CH_2$ may be replaced with O, S, $NR_{11}$, or other groups;

X is selected from the group consisting of O, S, $NR_{11}$, and NH;

Z, $R_x$, and

are defined as supra.

As used herein, the term "HA" is nothing or a pharmaceutically acceptable acid, e.g. hydrochloride, hydrobromide, hydroiodide, nitric acid, sulfic acid, bisulfic acid, phosphoric acid, phosphorous acid, phosphonic acid, isonicotinic acid, acetic acid, lactic acid, salicylic acid, citric acid, tartaric acid, pantothenic acid, bitartaric acid, ascorbic acid, succinic acid, maleic acid, gentisinic acid, fumaric acid, gluconic acid, glucaronic acid, saccharic acid, formic acid, benzoic acid, glutamic acid, methanesulfonic acid, ethanesulfonic acid, benzenesulfonic acid, p-toluenesulfonic acid and pamoic acid.

As used herein, "A" or "A⁻" is nothing or a pharmaceutically acceptable anion, e.g. Cl—, Br—, F—, I—, acetylsalicylate, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate or any pharmaceutically acceptable anion.

In certain embodiments, the functional unit of a HPP or HPC comprises a moiety of a prostaglandin or prostaglandin analog, including stereoisomers and pharmaceutically acceptable salts thereof, wherein the prostaglandin or the prostaglandin related compound is selected from the group consisting of $PGA_1$, $PGA_2$, $PGA_3$, $PGB_1$, $PGB_2$, $PGB_3$, $PGD_1$, $PGD_2$, $PGD_3$, $PGE_1$, $PGE_2$, $PGE_3$, $PGF_{1\alpha}$, $PGF_{1\beta}$, $PGF_{2\alpha}$, $PGF_{2\beta}$, $PGF_{3\alpha}$, $PGG_2$, $PGH_1$, $PGH_2$, $PGI_2$ (prostacyclin), $PGI_3$, $PGJ_2$, $PGK_1$, $PGK_2$, carboprost, prostalene, misoprostol, gemeprost, sulprostone, fluprostenol, cloprostenol, bimatoprost {(Z)-7-[(1R,2R,3R,5S)-3,5-Dihydroxy-2-[1E,3S]-3-hydroxy-5-phenyl-1-pentenyl]cyclopentyl}-5-N-ethylheptenamide}, latanoprost (13,14-dihydro-17-phenyl-18,19,20-trinor $PGF_{2\alpha}$ isopropyl ester), travoprost {(Z)-7-[(1R,2R,3R,5S)-3,5-dihydroxy-2-[(1E,3R)-3-hydroxy-4-[(α,α,α-trifluoro-m-tolyl)oxy]-1-butenyl]cyclopentyl]-5-heptenoate}, and unoprostone (13,14-dihydro-15-keto-20-ethyl $PGF_{2\alpha}$).

In certain embodiments, the functional unit of a HPP or HPC of the invention includes an inactive form of a prostaglandin or prostaglandin analog, including stereoisomers and pharmaceutically acceptable salts thereof, which is selected from the group consisting of $PGA_1$, $PGA_2$, $PGA_3$, $PGB_1$, $PGB_2$, $PGB_3$, $PGD_1$, $PGD_2$, $PGD_3$, $PGE_1$, $PGE_2$, $PGE_3$, $PGF_{1\alpha}$, $PGF_{1\beta}$, $PGF_{2\alpha}$, $PGF_{2\beta}$, $PGF_{3\alpha}$, $PGG_2$, $PGH_1$, $PGH_2$, $PGI_2$ (prostacyclin), $PGI_3$, $PGJ_2$, $PGK_1$, $PGK_2$, carboprost, prostalene, misoprostol, gemeprost, sulprostone, fluprostenol cloprostenol, bimatoprost {(Z)-7-[(1R,2R,3R,5S)-3,5-Dihydroxy-2-[1E,3S]-3-hydroxy-5-phenyl-1-pentenyl]cyclopentyl}-5-N-ethylheptenamide}, latanoprost (13,14-dihydro-17-phenyl-18,19,20-trinor $PGF_{2\alpha}$ isopropyl ester), travoprost {(Z)-7-[(1R,2R,3R,5S)-3,5-dihydroxy-2-[(1E,3R)-3-hydroxy-4-[(α,α,α-trifluoro-m-tolyl)oxy]-1-butenyl]cyclopentyl]-5-heptenoate}, and unoprostone (13,14-dihydro-15-keto-20-ethyl $PGF_{2\alpha}$).

II. Pharmaceutical Compositions Comprising HPPs

Another aspect of the invention relates to a pharmaceutical composition comprising at least one HPP of a prostaglandin or prostaglandin analog, and a pharmaceutically acceptable carrier.

The term "pharmaceutically acceptable carrier" as used herein means a pharmaceutically-acceptable material, composition or vehicle, such as a liquid or solid filler, diluent, excipient, solvent or encapsulating material, involved in carrying or transporting a HPP from one location, body fluid, tissue, organ (interior or exterior), or portion of the body, to another location, body fluid, tissue, organ, or portion of the body.

Each carrier is "pharmaceutically acceptable" in the sense of being compatible with the other ingredients, e.g., a HPP, of the formulation and suitable for use in contact with the tissue or organ of a biological system without excessive toxicity, irritation, allergic response, immunogenicity, or other problems or complications, commensurate with a reasonable benefit/risk ratio.

Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) alcohol, such as ethyl alcohol and propane alcohol; (20) phosphate buffer solutions; and (21) other non-toxic compatible substances employed in pharmaceutical formulations such as acetone.

The pharmaceutical compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like.

In one embodiment, the pharmaceutically acceptable carrier is an aqueous carrier, e.g. buffered saline and the like. In certain embodiments, the pharmaceutically acceptable carrier is a polar solvent, e.g. acetone and alcohol.

The concentration of HPP in these formulations can vary widely, and will be selected primarily based on fluid volumes, viscosities, body weight and the like in accordance with the particular mode of administration selected and the biological system's needs. For example, the concentration can be 0.001% to 100%, 0.1% to 80%, 1% to 70%, 1% to 50%, 1% to 30%, 1% to 10%, wt.

The compositions of the invention can be administered for prophylactic, therapeutic, and/or hygienic use. Such administration can be topical, mucosal, e.g., oral, nasal, vaginal, rectal, parenteral, transdermal, subcutaneous, intramuscular, intravenous, via inhalation, ophthalmic and other convenient routes. The pharmaceutical compositions can be administered in a variety of unit dosage forms depending upon the method of administration. For example, unit dosage forms suitable for oral administration include powder, tablets, pills, capsules and lozenges.

Thus, a typical pharmaceutical composition for intravenous administration would be about $10^{-9}$ g to about 100 g, about $10^{-6}$ g to about 100 g, about 0.001 g to about 100 g, or about 0.01 g to about 10 g per subject per day. Dosages from about 0.01 mg, up to about 5 g, per subject per day may be used. Actual methods for preparing parenterally administrable compositions will be known or apparent to those skilled in the art and are described in more detail in such publications as Remington's Pharmaceutical Science, 15th ed., Mack Publishing Company, Easton, Pa. (1980).

III. Applications of HPPs i) Methods for Penetrating a Biological Barrier.

Another aspect of the invention relates to a method of using a composition of the invention in penetrating one or more biological barriers in a biological subject. The method comprises a step of administrating to a biological barrier in the biological subject a HPP or a pharmaceutical composition of the invention. In one embodiment, a HPP shows more than 50 times or higher (about >100 times or higher, >about 200 times or higher, >about 300 times or higher, about >500 times or higher, >about 1,000 times or higher, >about 10,000 times or higher) penetration rate through one or more biological barriers than the penetration rate of its parent drug.

The term "biological barrier" as used herein refers to a biological layer that separates an environment into different spatial areas or compartments, which separation is capable of modulating (e.g. restricting, limiting, enhancing or taking no action in) the passing through, penetrating or translocation of substance or matter from one compartment/area to another. The different spatial areas or compartments as referred to herein may have the same or different chemical or biological environment(s). The biological layer as referred herein includes, but is not limited to, a biological membrane, a layer of cells, a biological structure, an inner surface of subjects, organisms, organs or body cavities, an external surface of subjects, organisms, organs or body cavities, or any combination or plurality thereof.

Examples of a biological membrane include a lipid bilayer structure, eukaryotic cell membrane, prokaryotic cell membrane, intracellular membrane (e.g., nucleus or organelle membrane, such as membrane or envelope of Golgi apparatus, rough and smooth endoplasmic reticulum (ER), ribosomes, vacuoles, vesicles, liposomes, mitochondria, lysosome, nucleus, chloroplasts, plastids, peroxisomes or microbodies).

The lipid bilayer referred to herein is a double layer of lipid-class molecules, including, but not limited to, phospholipids and cholesterol. In a particular embodiment, lipids for bilayer are amphiphilic molecules consisting of polar head groups and non-polar fatty acid tails. The bilayer is composed of two layers of lipids arranged so that their hydrocarbon tails face one another to form an oily core held together by the hydrophobic effect, while their charged heads face the aqueous solutions on either side of the membrane. In another particular embodiment, the lipid bilayer may contain one or more embedded protein and/or sugar molecule(s).

Examples of a cell layer include a lining of eukaryotic cells (e.g., epithelium, lamina propria and smooth muscle or muscularis mucosa (in gastrointestinal tract), a lining of prokaryotic cells (e.g., surface layer or S-layer which refers to a two dimensional structure monomolecular layer composed of identical proteins or glycoproteins, specifically, an S-layer refers to a part of a cell envelope commonly found in bacteria and archaea), a biofilm (a structured community of microorganisms encapsulated within a self-developed polymeric matrix and adherent to a living or inert surface), and a plant cell layer (e.g., epidermis). The cells may be normal cells or pathological cells (e.g. disease cells, cancer cells).

Examples of biological structures include structures sealed by tight or occluding junctions which provide a barrier to the entry of toxins, bacteria and viruses, e.g. the blood milk barrier and the blood brain barrier (BBB). In particular, BBB comprises an impermeable class of endothelium, which presents both a physical barrier through tight junctions adjoining neighboring endothelial cells and a transport barrier comprised of efflux transporters. The biological structure may also include a mixture of cells, proteins and sugars (e.g. blood clots).

Examples of inner surface of subjects, organisms, organs or body cavities include buccal mucosa, esophageal mucosa, gastric mucosa, intestinal mucosa, olfactory mucosa, oral mucosa, bronchial mucosa, uterine mucosa and endometrium (the mucosa of the uterus, inner layer of the wall of a pollen grain or the inner wall layer of a spore), or a combination or plurality thereof.

Examples of external surface of an subjects, organisms, organs or body cavities include capillaries (e.g. capillaries in the heart tissue), mucous membranes that are continuous with skin (e.g. such as at the nostrils, the lips, the ears, the genital area, and the anus) outer surface of an organ (e.g. liver, lung, stomach, brain, kidney, heart, ear, eye, nose, mouth, tongue, colon, pancreas, gallbladder, duodenum, rectum stomach, colonrectum, intestine, vein, respiratory system, vascular, the anorectum and pruritus ani), skin, cuticle (e.g., dead layers of epidermal cells or keratinocytes or superficial layer of overlapping cells covering the hair shaft of an animal, a multi-layered structure outside the epidermis of many invertebrates, plant cuticles or polymers cutin and/or cutan), external layer of the wall of a pollen grain or the external wall layer of a spore), or a combination or plurality thereof.

In addition, a biological barrier further includes a sugar layer, a protein layer or any other biological layer, or a combination or plurality thereof. For example, skin is a biological barrier that has a plurality of biological layers. A skin comprises an epidermis layer (outer surface), a dermis layer and a subcutaneous layer. The epidermis layer contains several layers including a basal cell layer, a spinous cell layer, a granular cell layer, and a stratum corneum. The stratum corneum ("horny layer") is the outmost layer of the epidermis, wherein cells here are flat and scale-like ("squamous") in shape. These cells contain a lot of keratin and are arranged in overlapping layers that impart a tough and oilproof and waterproof character to the skin's surface.

ii) Methods for Diagnosing a Condition in a Biological System.

Another aspect of the invention relates to a method of using a composition of the invention in diagnosing a condition in a biological system or subject. The method comprises the following steps:

1) administering a composition comprising a HPP to the biological system or subject;
2) detecting the presence, location or amount of the HPP or the functional unit of the HPP in the biological system or subject; and
3) determining a condition in the biological system or subject.

In certain embodiments, the HPP (or the agent cleaved from the HPP) aggregates in the site of action where a condition occurs. In certain embodiments, the presence, location or amount of the functional unit of the HPP is also detected. In certain embodiments, the onset, development, progress, or remission of a condition (e.g., a disease) associated is also determined.

In certain embodiments, the HPP is labeled with or conjugated to a detectable agent. Alternatively, the HPP is prepared to include radioisotopes for detection. Numerous detectable agents are available which can be generally grouped into the following categories:

(a) Radioisotopes, such as $^{35}S$, $^{14}C$, $^{13}C$, $^{15}N$, $^{125}I$, $^{3}H$, and $^{131}I$. The diagnostic agent can be labeled with the radioisotope using the techniques known in the art and radioactivity can be measured using scintillation counting; in addition, the diagnostic agent can be spin labeled for electron paramagnetic resonance for carbon and nitrogen labeling.

(b) Fluorescent agents such as BODIPY, BODIPY analogs, rare earth chelates (europium chelates), fluorescein and its derivatives, FITC, 5,6-carboxyfluorescein, rhodamine and its derivatives, dansyl, Lissamine, phycoerythrin, green fluorescent protein, yellow fluorescent protein, red fluorescent protein and Texas Red. Fluorescence can be quantified using a fluorometer.

(c) Various enzyme-substrate agents, such luciferases (e.g., firefly luciferase and bacterial luciferase), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Examples of enzyme-substrate combinations include, for example: (i) Horseradish peroxidase (HRPO) with hydrogen peroxidase as a substrate, wherein the hydrogen peroxidase oxidizes a dye precursor (e.g., orthophenylene diamine (OPD) or 3,3', 5,5'-tetramethyl benzidine hydrochloride (TMB)); (ii) alkaline phosphatase (AP) with para-Nitrophenyl phosphate as chromogenic substrate; and (iii) β-D-galactosidase (β-D-Gal) with a chromogenic substrate (e.g., p-nitrophenyl-β-D-galactosidase) or fluorogenic substrate 4-methylumbelliferyl-β-D-galactosidase.

In certain embodiments, the detectable agent is not necessarily conjugated to the diagnostic agent but is capable of recognizing the presence of the diagnostic agent and the diagnostic agent can be detected.

In certain embodiments, the HPP of the invention can be provided in a kit, i.e., a packaged combination of reagents in predetermined amounts with instructions for performing the diagnostic assay. Where the HPP is labeled with an enzyme, the kit will include substrates and cofactors required by the enzyme (e.g., a substrate precursor which provides the detectable chromophore or fluorophore). In addition, other additives may be included such as stabilizers, buffers (e.g., a block buffer or lysis buffer) and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

iii) Methods for Screening a Substance for a Desired Character

Another aspect of the invention relates to a method of screening a HPP for a desired nature or character.

In certain embodiments, the method comprises:
1) covalently linking a test functional unit to a transportational unit through a linker to form a test composition (or covalently linking a functional unit to a test transportational unit through a linker, or covalently linking a functional unit to a transportational unit through a test linker)
2) administering the test composition to a biological system or subject; and
3) determining whether the test composition has the desired nature or character.

In one embodiment, the desired character may include, for example, 1) the ability of the test functional unit to form a high penetration composition or convert back to a parent drug, 2) the penetration ability and/or rate of the test composition, 3) the efficiency and/or efficacy of the test composition, 4) the transportational ability of the test transportational unit, and 5) the cleavability of the test linker.

iv) Methods for Treating a Condition in a Biological Subject

Another aspect of the invention relates to a method for treating a condition in a biological system or subject by administering a HPP or pharmaceutical composition of the invention to the biological system or subject.

The term "treating" as used herein means curing, alleviating, inhibiting, reducing, or preventing. The term "treat" as used herein means cure, alleviate, inhibit, reduce or prevent. The term "treatment" as used herein means cure, alleviation, inhibition, reduction or prevention.

The term "biological system," "biological subject" or "subject" as used herein means an organ, a group of organs that work together to perform a certain task, an organism, or a group of organisms. The term "organism" as used herein means an assembly of molecules that function as a more or less stable whole and has the properties of life, such as animal, plant, fungus, or micro-organism.

The term "animal" as used herein means an eukaryotic organism characterized by voluntary movement. Examples of animal include, without limitation, vertebrata (e.g. human, mammals, birds, reptiles, amphibians, fishes, marsipobranchiata and leptocardia), tunicata (e.g. thaliacea, appendicularia, sorberacea and ascidioidea), articulata (e.g. Insecta, Myriapoda, Malacapoda, arachnida, pycnogonida, merostomata, crustacea and annelida), Gehyrea (Anarthropoda), helminthes (e.g. rotifera).

The term "plant" as used herein means organisms belonging to the kingdom Plantae. Examples of plant include, without limitation, seed plants, bryophytes, ferns and the fern allies. Examples of seed plants include, without limitation, cycads, ginkgo, conifers, gnetophytes, angiosperms. Examples of bryophytes include, without limitation, liverworts, hornworts and mosses. Examples of ferns include, without limitation, Ophioglossales (e.g. adders-tongues, moonworts, and grape-ferns), Marattiaceae and the leptosporangiate ferns. Examples of fern allies include, without limitation, lycopsida (e.g. the clubmosses, spikemosses and quillworts), the Psilotaceae (e.g. the Lycopodiophyta and the whisk ferns) and the Equisetaceae (e.g. horsetails).

The term "fungus" as used herein means a eukaryotic organism that is a member of the kingdom Fungi. Examples of fungus include, without limitation, chytrids, blastocladiomycota, neocallimastigomycota, zygomycota, glomeromycota, ascomycota and basidiomycota.

The term "micro-organism" as used herein means an organism that is microscopic (e.g. with length scale of micrometer), Examples of micro-organism include, without limitation, bacteria, fungi, archaea, protists and microscopic plants (e.g. green algae) and microscopic animals (e.g. plankton, planarian and amoeba).

Some examples of the conditions that the methods can treat include conditions that can be treated by the parent drug of a HPP.

v). Methods of Using HPPs of Prostaglandins or Prostaglandin Analogs, or Pharmaceutical Compositions Thereof in Treatments.

Another aspect of the invention relates to a method of using HPP of prostaglandins or prostaglandin analogs, or a pharmaceutical composition thereof in treating a condition in a biological system or subject by administrating the HPP of prostaglandins or prostaglandin analogs, or a pharmaceutical composition thereof to the biological system or subject.

A) Conditions Treatable by Methods of the Invention

Examples of the conditions or diseases that can be treated by the method of the invention include:
1) abnormal birth or reproduction of a human or animal, e.g., inducing childbirth (parturition) or abortion (e.g., $PGE_2$ or $PGF_2$, used with or without mifepristone, which is a progesterone antagonist) and treating egg binding in small birds;
2) peptic ulcers (PGE);
3) severe Raynaud's phenomenon or ischemia of a limb (e.g., iloprost, cisaprost);
4) abnormal blood pressure, e.g. hypertension, hypotension, and pulmonary hypertension;
5) cardiovascular conditions or dysfunction, e.g., inhibiting aggregation of platelets, closure of patent ductus arteriosus in newborns with particular cyanotic heart defects (PGE1), heart attack, unstable angina, peripheral occlusive arterial disease and stroke;
6) eye disease, e.g., glaucoma (e.g., in form of bimatoprost ophthalmic solution, which is a synthetic prostamide analog with ocular hypotensive activity), ocular hypertension, loss of vision after ophthalmic surgery, vision of a warm-blooded animal impaired by cystoid macular edema and cataract;
7) sexual dysfunctions, e.g., erectile dysfunction, penile rehabilitation following surgery (e.g., $PGE_1$ as alprostadil) or female sexual dysfunction;
8) bone diseases, e.g. osteoporosis, Paget's disease and bone metastases,
9) gastrointestinal conditions,
10) inflammation,
11) shock, and
12) infertility.

In particular, prostaglandins and prostaglandin analogs (e.g., iloprost, cisaprost) can be used as a vasodilator in severe Raynaud's phenomenon or ischemia of a limb or in pulmonary hypertension, traditionally via intravenous, subcutaneous or inhalation administration routes. Iloprost, cisaprost are a leading class of glaucoma drugs with a proven safety and efficacy for controlling intraocular pressure (IOP). PGE2 stimulates osteoblasts to release factors which stimulate bone resorption by osteoclasts. When administered intravaginally, $PGE_2$ will stimulate the endometrium of the gravid uterus to contract in a manner similar to uterine contractions observed during labor. Thus, $PGE_2$ is therapeutically available as dinoprostone (prostin $E_2$, Upjohn) for use as an abortifacient. $PGE_2$ is also a potent stimulator of smooth muscle of the gastrointestinal (GI) tract and can elevate body temperature in addition to possessing potent vasodilating properties in most vascular tissue and also possessing constrictor effects at certain sites. $PGF_{2\alpha}$ shares many of PGEs' properties and is also therapeutically available as an abortifacient (Prostin F2 alpha, Upjohn). The synthetic 15-methyl derivative of $PGF_{2\alpha}$, carboprost, is also therapeutically available as an abortifacient (Prostin 15/M, Upjohn). $PGD_2$ causes both vasodilation and vasoconstriction. Whereas the PGEs produce a relaxation of bronchial and tracheal smooth muscle, PGFs and PGD2 cause contraction. $PGE_1$ is available as alprostadil to maintain potency of the ductus arteriosus in neonates until surgery can be performed to correct congenital heart defects. $PGE_1$ and its analogs may be used for the treatment of male erectile dysfunction (Yeager, James L. U.S. Pat. No. 6,693,135) and enhancing female sexual arousal (Scott, Nathan Earl, U.S. Pat. No. 6,291,528).

It has been known that prostaglandin $I_2$ ($PGI_2$, i.e., prostacyclin) has the functions of vasodilation, inhibiting platelet aggregation, and bronchodilatation; prostaglandin $E_2$ ($PGE_2$) has the functions of bronchoconstriction, gastraintestinal tract smooth muscle contraction, gastraintestinal tract smooth muscle relaxation, vasodilatation, reducing or inhibiting gastric acid secretion, enhancing or increasing gastric mucus secretion, uterus contraction (when pregnant), lipolysis inhibition, enhancing or increasing autonomic neurotransmitters, hyperalgesia and pyrogenic agent; prostaglandin $F_{2\alpha}$ ($PGF_{2\alpha}$) has the functions of uterus contraction and bronchoconstriction.

In certain embodiments, the method of treating a condition in a subject amelioratable or treatable with prostaglandins or prostaglandins analogs comprising administering a HPP or HPC of prostaglandins or prostaglandins analogs, or a pharmaceutical composition thereof to the subject. Examples of the condition include, for instance, reproduction disease or abnormal birth of a human or animal (e.g., abortion), peptic ulcers, severe Raynaud's phenomenon or ischemia of a limb, abnormal blood pressure (systemic high blood pressure and hypotensive control), cardiovascular diseases or dysfunction (e.g., for inhibition of platelet aggregation), eye disease (e.g. glaucoma or ocular hypertension), sexual dysfunctions (e.g., male erectile dysfunction and female sex dysfunction) and bone diseases, pulmonary diseases, gastrointestinal disease, inflammation, shock and fertility.

In one embodiment, a HPP of a prostaglandin or prostaglandin analog shows better or similar therapeutic activities comparing to its parent drug.

B) Administration of the Compositions According to the Invention.

A HPP or a pharmaceutical composition thereof can be administered to a biological system by any administration route known in the art, including without limitation, oral, enteral, buccal, nasal, topical, rectal, vaginal, aerosol, transmucosal, epidermal, transdermal, dermal, ophthalmic, pulmonary, subcutaneous, and/or parenteral administration. The pharmaceutical compositions can be administered in a variety of unit dosage forms depending upon the method of administration.

A parenteral administration refers to an administration route that typically relates to injection which includes but is not limited to intravenous, intramuscular, intraarterial, intrathecal, intracapsular, intraorbital, intra cardiac, intradermal, intraperitoneal, transtracheal, subcutaneous, subcuticular, intraarticular, subcapsular, subarachnoid, intraspinal, and/or intrasternal injection and/or infusion.

A HPP or a pharmaceutical composition thereof can be given to a subject in the form of formulations or preparations suitable for each administration route. The formulations useful in the methods of the invention include one or more HPPs, one or more pharmaceutically acceptable carriers therefor, and optionally other therapeutic ingredients. The formulations may conveniently be presented in unit dosage form and may be prepared by any methods well known in the art of pharmacy. The amount of active ingredient which can be combined with a carrier material to produce a single dosage form will vary depending upon the subject being treated and the particular mode of administration. The amount of a HPP which can be combined with a carrier material to produce a pharmaceutically effective dose will generally be that amount of a HPP which produces a therapeutic effect. Generally, out of one hundred percent, this amount will range from about 1 percent to about ninety-nine percent of the HPP, preferably from about 20 percent to about 70 percent.

Methods of preparing these formulations or compositions include the step of bringing into association a HPP with one or more pharmaceutically acceptable carriers and, optionally, one or more accessory ingredients. In general, the formulations are prepared by uniformly and intimately bringing into association a HPP with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a HPP as an active ingredient. A compound may also be administered as a bolus, electuary, or paste.

In solid dosage forms for oral administration (e.g., capsules, tablets, pills, dragees, powders, granules and the like), the HPP is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate, (5) solution retarding agents, such as paraffin, (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered peptide or peptidomimetic moistened with an inert liquid diluent. Tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of a HPP therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain pacifying agents and may be of a composition that they release the HPP(s) only, or preferentially, in a certain portion of the gastrointestinal tract, optionally, in a delayed manner. Examples of embedding compositions which can be used include polymeric substances and waxes. The HPP can also be in micro-encapsulated form, if appropriate, with one or more of the above-described excipients.

Liquid dosage forms for oral administration include pharmaceutically acceptable emulsions, microemulsions, solutions, suspensions, syrups and elixirs. In addition to the HPP, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming and preservative agents.

Suspensions, in addition to the HPP, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more HPPs with one or more suitable non-irritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent. Formulations which are suitable for vaginal administration also include pessaries, tampons, creams, gels, pastes, foams or spray formulations containing such carriers as are known in the art to be appropriate.

Formulations for the topical or transdermal or epidermal or dermal administration of a HPP composition include powders, sprays, ointments, pastes, creams, lotions, gels, solutions, patches and inhalants. The active component may be mixed under sterile conditions with a pharmaceutically acceptable carrier, and with any preservatives, buffers, or propellants which may be required. The ointments, pastes, creams and gels may contain, in addition to the HPP composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays can contain, in addition to the HPP composition, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The HPP composition can be alternatively administered by aerosol. This is accomplished by preparing an aqueous aerosol, liposomal preparation or solid particles containing the HPPs. A nonaqueous (e.g., fluorocarbon propellant) suspension could be used. Sonic nebulizers can also be used. An aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids (such as glycine), buffers, salts, sugars or sugar alcohols. Aerosols generally are prepared from isotonic solutions.

Transdermal patches can also be used to deliver HPP compositions to a site of condition or disease. Such formulations can be made by dissolving or dispersing the agent in the proper medium. Absorption enhancers can also be used to increase the flux of the peptidomimetic across the skin. The rate of such flux can be controlled by either providing a rate controlling membrane or dispersing the peptidomimetic in a polymer matrix or gel.

Ophthalmic formulations, eye ointments, powders, solutions and the like, are also contemplated as being within the scope of this invention.

Formulations suitable for parenteral administration comprise a HPP in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the formulations suitable for parenteral administration include water, ethanol, polyols (e.g., such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

Formulations suitable for parenteral administration may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Injectable depot forms are made by forming microencapsule matrices of a HPP or in biodegradable polymers such as polylactide-polyglycolide. Depending on the ratio of the HPP to polymer, and the nature of the particular polymer employed, the rate of drug release can be controlled. Examples of other biodegradable polymers include poly (orthoesters) and poly (anhydrides). Depot injectable formulations are also prepared by entrapping the HPP in liposomes or microemulsions which are compatible with body tissue.

In an embodiment of the invention, a HPP composition is delivered to a disease or infection site in a therapeutically effective dose. As is known in the art of pharmacology, the precise amount of the pharmaceutically effective dose of a HPP that will yield the most effective results in terms of efficacy of treatment in a given patient will depend upon, for example, the activity, the particular nature, pharmacokinetics, pharmacodynamics, and bioavailability of a particular HPP, physiological condition of the subject (including race, age, sex, weight, diet, disease type and stage, general physical condition, responsiveness to a given dosage and type of medication), the nature of pharmaceutically acceptable carriers in a formulation, the route and frequency of administration being used, and the severity or propensity of a disease caused by pathogenic target microbial organisms, to name a few. However, the above guidelines can be used as the basis for fine-tuning the treatment, e.g., determining the optimum dose of administration, which will require no more than routine experimentation consisting of monitoring the subject and adjusting the dosage. Remington: *The Science and Practice of Pharmacy* (Gennaro ed. 20th Ed., Williams & Wilkins Pa., USA, 2000).

IV. Advantages

In certain embodiments, since the HPP of the invention is capable of crossing one or more biological barriers, the HPP can be administered locally (e.g., typically or transdermally) to reach a location where a condition occurs without the necessity of a systematic administration (e.g., oral or parenteral administration). The local administration and penetration of the HPP allows the HPP to reach the same level of local concentration of an agent or drug with much less amount or dosage of HPP in comparison to a systematic administration of a parent agent or drug, alternatively, a higher level of local concentration which may not be afforded in the systematic administration, or if possible, requires significantly higher dosage of an agent in the systematic administration. The high local concentration of the HPP or its parent agent if being cleaved enables the treatment of a condition more effectively or much faster than a systematically delivered parent agent and the treatment of new conditions that may not be possible or observed before. The local administration of the HPP may allow a biological subject to reduce potential sufferings from a systemic administration, e.g., adverse reactions associated with the systematic exposure to the agent, gastrointestinal/renal effects. Additionally, the local administration may allow the HPP to cross a plurality of biological barriers and reach systematically through, for example, general circulation and thus avoid the needs for systematic administration (e.g., injection) and obviate the pain associated with the parenteral injection.

In certain embodiments, the HPP according to the invention can be administered systematically (e.g., orally or parenterally). The HPP or the active agent (e.g., drug or metabolite) of the HPP may enter the general circulation with a faster rate than the parent agent and gain faster access to the action site a condition. Additionally, the HPP can cross a biological barrier (e.g., brain biological barrier) which has not been penetrated if a parent agent is administered and thus offer novel treatment of conditions that may not be possible or observed before.

For example, the HPPs of prostaglandins or prostaglandin analogs of the invention exhibit higher penetration rate through a biological barrier (e.g., about >10 times, about >50 times, >about 100 times, about >200 times, about >300 times, about >500 times, about >1,000 times, about >10,000 times or higher than the penetration rate of prostaglandins or prostaglandin analogs if administered alone). No side effect was observed from the subjects who/which were administered a HPP of a prostaglandin or prostaglandin analog, while side effects were observed from the subjects to whom/which the parent prostaglandin or a related compound or analog thereof was administered at the similar dosage. The side effects of prostaglandins or prostaglandin analogs include, but are not limited to, pain, itching, or swelling of the eye; penile pain; minor urethral trauma; a sensation of urethral burning or pain; cavernous sinus aching in the genital area; overdosing caused by transurethral delivery PGs and the delivery of excess PGs to the vagina of the partner; and pain, an incidence of fibrosis and scar formation at the site caused by injection administration route.

V. Examples

The following examples are provided to better illustrate the claimed invention and are not to be interpreted in any way as limiting the scope of the invention. All specific compositions, materials, and methods described below, in whole or in part, fall within the scope of the invention. These specific compositions, materials, and methods are not intended to limit the invention, but merely to illustrate specific embodiments falling within the scope of the invention. One skilled in the art may develop equivalent compositions, materials, and methods without the exercise of inventive capacity and without departing from the scope of the invention. It will be understood that many variations can be made in the procedures herein described while still remaining within the bounds of the invention. It is the intention of the inventors that such variations are included within the scope of the invention.

Example 1

Preparation of a HPP from a Parent Drug

In certain embodiments, a parent compound having the following Structure P:

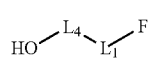

Structure P is converted to a HPP having Structure L:

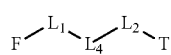

Structure L including stereoisomers and pharmaceutically acceptable salts thereof, wherein:

F, $L_1$, $L_2$, $L_4$ and T are defined the same as supra;

In certain embodiments of the invention, a HPP having Structure L is prepared according to the conventional organic synthesis by reacting the parent compounds or derivatives of the parent compounds having Structure D (e.g. acid halides, mixed anhydrides of the parent compounds, etc.):

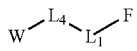

Structure D with compounds of Structure E (Scheme 1):

T-L$_2$-H   Structure E wherein W is selected from the group consisting of OH, halogen, alkoxycarbonyl and substituted aryloxycarbonyloxy; and F, T, L$_1$, L$_2$, and L$_4$ are defined the same as supra.

Scheme 1. Preparation of a HPP from a parent compound.

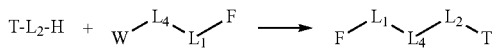

Preparation of N,N-diethylaminoethyl 11,15-dihydroxy-9-oxoprost-13-en-1-oate.AcOH 37.7 g (0.1 mol) of sodium 11,15-dihydroxy-9-oxoprost-13-en-1-oate was dissolved in 100 ml of acetonitrile. 26.1 g (0.1 mol) of 2-Bromo-N,N-diethylethylamine.HBr and 8.6 g of sodium bicarbonate were added into the reaction mixture. The mixture was stirred for overnight at RT. The solvents were evaporated off. 250 ml of ethyl acetate was added into the reaction mixture and the mixture was washed with water (3×100 ml). The organic solution was dried over anhydrous sodium sulfate. Sodium sulfate was removed by filtration. 6 g of acetic acid was added into the reaction mixture with stirring. Hexane (200 ml) was added. The solid product was collected by filtration. After drying, it yielded 42 g of the desired product (81.8%). Hygroscopic product; Solubility in water: 100 mg/ml; Elementary analysis: C28H51NO7; MW: 513.37. Calculated % C, 65.47; H, 10.01; N, 2.73; O, 21.80. Found % C, 65.42; H, 10.03; N, 2.70; O, 21.85.

Preparation of N,N-diethylaminoethyl 11,15-diacetoxy-9-oxoprosta-5,13-dien-1-oamide.AcOH 43.7 g (0.1 mol) of 11,15-diacetoxy-9-oxoprosta-5,13-dien-1-oic acid was dissolved in 300 ml of chloroform. 20.6 g of N,N'-Dicyclohexylcarbodiimide was added into the reaction mixture. 11.7 g of N,N-diethylaminoethylamine was added into the reaction mixture. The mixture was stirred for 3 hours at RT. The solid was removed by filtration. The chloroform solution was washed with 5% NaHCO$_3$ (2×100 ml) and water (3×100 ml). The organic solution was dried over anhydrous sodium sulfate. Sodium sulfate was removed by filtration. 6 g of acetic acid was added into the reaction mixture with stirring. Hexane (200 ml) was added. The solid product was collected by filtration. After drying, it yielded 45 g of the desired product (85.8%). Hygroscopic product; Solubility in water: 100 mg/ml; Elementary analysis: C$_{34}$H$_{59}$NO$_9$S; MW: 657.90. Calculated % C, 62.07; H, 9.04; N, 2.13; O, 21.89; S, 4.87. Found % C, 62.02; H, 9.06; N, 2.11; O, 21.95; S, 4.86.

Preparation of S—(N,N-dimethylaminoethyl) 9,11,15-triacetoxythioprost-13-en-1-oate.AcOH 49.9 g (0.1 mol) of 9,11,15-triacetoxyprost-13-en-1-oic acid was dissolved in 300 ml of chloroform. 20.6 g of N,N'-Dicyclohexylcarbodiimide was added into the reaction mixture. 13.1 g of dimethylaminoethyl mercaptan was added into the reaction mixture. The mixture was stirred for 3 hours at RT. The solid was removed by filtration. The chloroform solution was washed with 5% NaHCO$_3$ (2×100 ml) and water (3×100 ml). The organic solution was dried over anhydrous sodium sulfate. Sodium sulfate was removed by filtration. 6 g of acetic acid was added into the reaction mixture with stirring. Hexane (200 ml) was added. The solid product was collected by filtration. After drying, it yielded 45 g of the desired product (85.8%). Hygroscopic product; Solubility in water: 100 mg/ml; Elementary analysis: C$_{32}$H$_{53}$NO$_9$; MW: 657.9 Calculated % C, 64.51; H, 8.97; N, 2.35; O, 24.17. Found % C, 64.47; H, 8.99; N, 2.34; O, 24.20.

Preparation of N,N-diethylaminoethyl 9,11,15-trihydroxyprosta-5,13-dien-1-oate.AcOH 37.7 g (0.1 mol) of sodium 9,11,15-trihydroxyprosta-5,13-dien-1-oate was dissolved in 100 ml of acetonitrile. 39 g (0.15 mol) of 2-Bromo-N,N-diethylethylamine.HBr in ethyl acetate was added into the reaction mixture. The mixture was stirred for 3 h at RT. Then 8 g of sodium bicarbonate was added into the reaction mixture. The mixture is stirred for another 2 h at RT. The solvents were evaporated off. 250 ml of ethyl acetate was added into the reaction mixture and the mixture was washed with water (3×100 ml). The organic solution was dried over anhydrous sodium sulfate. Sodium sulfate was removed by filtration. 6 g of acetic acid was added into the reaction mixture with stirring. Hexane (200 ml) was added. The solid product was collected by filtration. After drying, it yielded 45 g of the desired product (87.6%). Hygroscopic product; Solubility in water: 100 mg/ml; Elementary analysis: C$_{28}$H$_{51}$NO$_7$; MW: 513.71. Calculated % C, 65.47; H, 10.01; N, 2.73; O, 21.80. Found % C, 65.42; H, 10.03; N, 2.70; O, 21.85.

Preparation of N,N-diethylaminoethyl 9,11,15-trihydroxy-15-methylprosta-5,13-dien-1-oate.AcOH 60 g of Polymer-bound triethylamine (3 mol/g, 100-200 mesh) was suspended in 180 ml of chloroform. 29.6 g (0.1 mol) of N,N-diethylaminoethyl 9,11,15-trihydroxy-15-methylprosta-5,13-dien-1-oic acid was added into the mixture with stirring. 43 g (0.15 mol) of N,N-diethylaminoethyl bromide.HBr was added into the mixture and the mixture was stirred for 5 hours at RT. The polymer was removed by filtration and washed with tetrahydrofuran (3×50 ml). 8.2 g (0.1 mol) of sodium acetate was added into the reaction mixture with stirring. The mixture was stirred for 2 h. The solid was removed by filtration and washed with chloroform (3×50 ml). The solution was concentrated in vacuo to 100 ml. Then 300 ml of hexane was added into the solution. The solid product was collected by filtration and washed with hexane (3×100 ml). After drying, it yielded 47 g of the desired product (87.8%). Hygroscopic product; Solubility in water: 100 mg/ml; Elementary analysis: C$_{28}$H$_{51}$NO$_7$; MW: 527.73. Calculated % C, 66.00; H, 10.12; N, 2.65; O, 21.22. Found % C, 65.96; H, 10.15; N, 2.64; O, 21.24.

Example 3

HPPs have Higher In Vitro Penetration Rates Across Human Skin Comparing to Their Parent Drugs The penetration rates of HPPs and their parent drugs through human skin were measured in vitro by modified Franz cells. The Franz cells have two chambers, the top sample chamber and the bottom receiving chamber. The human skin tissue (360-400 μm thick) that separates the top and the receiving chambers was isolated from the anterior or posterior thigh areas.

Figure 2:
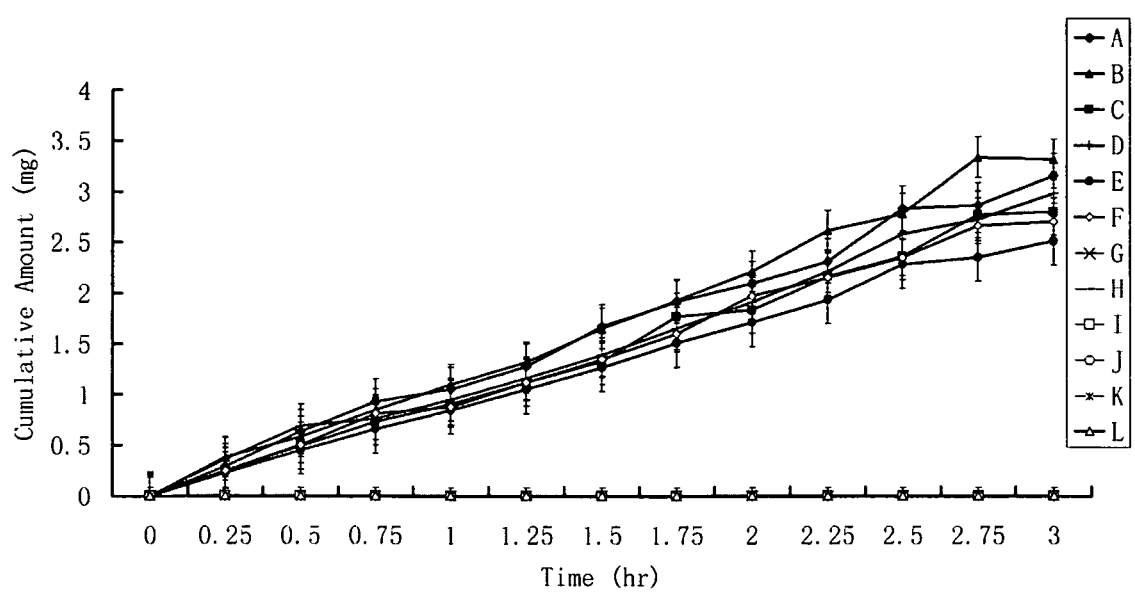
FIG. 2 depicts cumulative amounts of N,N-diethylaminoethyl 9,11-dihydroxy-15-keto-20-ethylprost-5,13-dien-1-oate.AcOH (A, 10% solution), N,N-diethylaminoethyl 11,16-dihydroxy-9-oxo-16-methylprost-13-en-1-oate.AcOH (B, 10% solution), N,N-diethylaminoethyl (Z)-7-{(1R,2R,3R,5S)-3,5-dihydroxy-2-[(1E,3R)-3-hydroxy-4-[(α,α,α-trifluoro-m-tolyl)oxy]-1-butenyl]cyclopentyl}-5-heptenoate.AcOH(C, 10% solution), N,N-diethylaminoethyl (Z)-7{(1R,2R,3R,5S)3,5-dihydroxy-2-[(3R)-3-hydroxy-5-phenylpentyl]cyclopentyl}-5-heptenoate.AcOH (D, 10% solution), N,N-diethylaminoethyl (Z)-7-{(1R,2R,3R,5S)-3,5-Dihydroxy-2-[(1E,3S)-3-hydroxy-5-phenyl-1-pentenyl]cyclopentyl}-heptenoate.AcOH (E, 10% solution), N,N-diethylaminoethyl 11,15-dihydroxy-16,16-dimethyl-9-oxoprosta-2,13-dien-1-oate.AcOH (F, 10% solution), unoprostone (G, 10% suspension), misoprostol (H, 10% suspension), travoprost (I, 10% suspension), latanoprost (J, 10% suspension), bimatoprost (K, 10% suspension), gemeprost, (L, 10% suspension), crossing isolated human skin tissue in Franz cells (n=5). In each case, the vehicle was pH 7.4 phosphate buffer (0.2 M).
Figure 3:
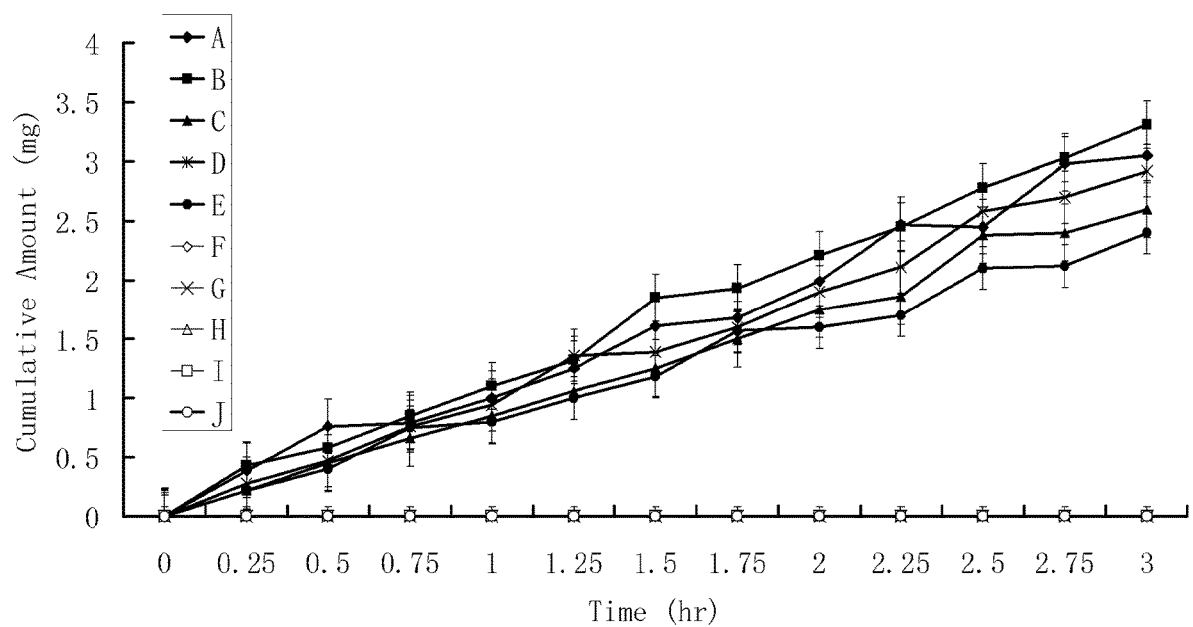
FIG. 3 depicts cumulative amounts of N,N-diethylaminoethyl 7-[3-hydroxy-2-(3-hydroxy-4-phenoxy-1-butenyl)-5-oxocyclopentyl]-5-heptenoate.AcOH (A, 10% solution), N,N-diethylaminoethyl 6,9-epoxy-11,15-dihydroxyprosta-5,13-dien-1-oate.AcOH (B, 10% solution), N,N-diethylaminoethyl 7-{3,5-dihydroxy-2-[3-hydroxy-4-(3-trifluoromethylphenoxy)-1-butenyl]cyclopentyl}-5-heptenoate.AcOH(C, 10% solution), N,N-diethylaminoethyl 7-{2-[4-(3-chlorophenoxy)-3-hydroxy-1-butenyl]-3,5-dihydroxycyclopentyl}-5-heptenoate.AcOH (D, 10% solution), N,N-diethylaminoethyl 7-[3,5-dihydroxy-2-(3-hydroxy-4-phenoxy-1-butenyl)cyclopentyl]-4,5-heptadien-1-oate.AcOH (E, 10% solution), sulprostone (F, 10% suspension), PGI$_2$ (G, 10% suspension), fluprostenol (H, 10% suspension), cloprostenol (I, 10% suspension), and fenprostalene (J, 10% suspension), crossing isolated human skin tissue in Franz cells (n=5). In each case, the vehicle was pH 7.4 phosphate buffer (0.2 M).

The compound tested (2 mL, 20% in 0.2 M phosphate buffer, pH. 7.4) were added to the sample chamber of a Franz cell. The receiving chamber contains 10 ml of 2% bovine serum albumin in saline which was stirred at 600 rpm. The cumulative amounts of the tested compounds penetrating the skin versus time were determined by high-performance liquid chromatography (HPLC) method. The results using a donor consisting of either a 10% solution of some of the prodrugs or a 10% suspension of parent drugs (e.g., prostaglandins, prostacyclin, and prostaglandin analogs) in 0.2 mL of pH 7.4-phosphate buffer (0.2M) are shown in FIGS. 1-3. The apparent flux values of the tested compounds are calculated from the slopes in FIGS. 1-3 and summarized in Table 1.

Because the lowest detectable apparent flux values in this method is 1 μg/cm$^2$/h, parent drugs that shows a apparent flux value less than 1 μg/cm$^2$/h are considered as not detectable for penetrating across the skin tissue. The HPPs of these parent drugs (e.g. PGE$_1$, PGE$_2$, PGF$_1\alpha$, PGF$_2\alpha$, Carboprost, Prostalene, Unoprostone, Misoprostol, Travoprost, Latanoprost, Bimatoprost, Gemeprost, Sulprostone, PGI$_2$, Fluprostenol and Cloprostenol) have detectable penetration across the skin tissue. For the parent drugs that have detectable apparent flux value, their HPPs have higher apparent flux value.

TABLE 1

In vitro Penetration Rate of Prostaglandins Prodrug Compounds and their Parent Compounds

| Prodrug compounds | mg/cm$^2$/h | Parent compounds | mg/cm$^2$/h |
|---|---|---|---|
| Prostaglandins | | | |
| N,N-diethylaminoethyl 11,15-dihydroxy-9-oxoprost-13-en-1-oate•AcOH | 1.01 | PGE$_1$ | 0.001 |
| N,N-diethylaminoethyl 11,15-dihydroxy-9-oxoprosta-5,13-dien-1-oate•AcOH | 1.10 | PGE$_2$ | 0.001 |
| N,N-diethylaminoethyl 9,11,15-trihydroxyprost-13-en-1-oate•AcOH | 0.85 | PGE$_1\alpha$ | 0.001 |
| N,N-diethylaminoethyl 9,11,15-trihydroxyprosta-5,13-dien-1-oate•AcOH | 0.94 | PGF$_2\alpha$ | 0.001 |
| N,N-diethylaminoethyl 9,11,15-trihydroxy-15-methylprosta-5,13-dien-1-oate•AcOH | 0.80 | Carboprost | 0.001 |
| N,N-diethylaminoethyl 9,11,15-trihydroxy-15-methylprosta-4,5,13-trien-1-oate•AcOH | 0.90 | Prostalene | 0.001 |
| N,N-diethylaminoethyl 9,11-dihydroxy-15-keto-20-ethylprost-5,13-dien-1-oate•AcOH (9,11-dihydroxy-15-keto-20-ethylprostaglandin F$_{2\alpha}$ N,N-diethylaminoethyl ester) | 1.05 | Unoprostone | 0.001 |
| N,N-diethylaminoethyl 11,16-dihydroxy-9-oxo-16-methylprost-13-en-1-oate•AcOH | 1.09 | Misoprostol | 0.001 |
| N,N-diethylaminoethyl (Z)-7-{(1R,2R,3R,5S)-3,5-dihydroxy-2-[(1E,3R)-3-hydroxy-4-[(α,α,α-trifluoro-m-tolyl)oxy]-1-butenyl]cyclopentyl}-5-heptenoate•AcOH | 0.91 | Travoprost | 0.001 |
| N,N-diethylaminoethyl (Z)-7{(1R,2R,3R,5S)3,5-dihydroxy-2-[(3R)-3-hydroxy-5-phenylpentyl]cyclopentyl}-5-heptenoate•AcOH | 0.95 | Latanoprost | 0.001 |
| N,N-diethylaminoethyl (Z)-7-{(1R,2R,3R,5S)3,5-Dihydroxy-2-[(1E,3S)-3-hydroxy-5-phenyl-1-pentenyl]cyclopentyl}-heptenoate•AcOH | 0.85 | Bimatoprost | 0.001 |
| N,N-diethylaminoethyl 11,15-dihydroxy-16,16-dimethyl-9-oxoprosta-2,13-dien-1-oate•AcOH | 0.88 | Gemeprost | 0.001 |
| N,N-diethylaminoethyl 7-[3-hydroxy-2-(3-hydroxy-4-phenoxy-1-butenyl)-5-oxocyclopentyl]-5-heptenoate•AcOH | 1.01 | Sulprostone | 0.001 |
| N,N-diethylaminoethyl 6,9-epoxy-11,15-dihydroxyprosta-5,13-dien-1-oate•AcOH | 1.11 | PGI$_2$ | 0.001 |
| N,N-diethylaminoethyl 7-{3,5-dihydroxy-2-[3-hydroxy-4-(3-trifluoromethylphenoxy)-1-butenyl]cyclopentyl}-5-heptenoate•AcOH | 0.86 | Fluprostenol | 0.001 |

TABLE 1-continued

In vitro Penetration Rate of Prostaglandins
Prodrug Compounds and their Parent Compounds

| Prodrug compounds | mg/cm$^2$/h | Parent compounds | mg/cm$^2$/h |
|---|---|---|---|
| N,N-diethylaminoethyl 7-{2-[4-(3-chlorophenoxy)-3-hydroxy-1-butenyl]-3,5-dihydroxycyclopentyl}-5-heptenoate•AcOH | 0.92 | Cloprostenol | 0.001 |
| N,N-diethylaminoethyl 7-[3,5-dihydroxy-2-(3-hydroxy-4-phenoxy-1-butenyl)cyclopentyl]-4,5-heptadien-1-oate•AcOH | 0.81 | fenprostalene | 0.001 |

Example 4

In Vivo Transportation of Prodrug and Application of the HPPs in the Treatments of Conditions A. Transportation of HPPs Through Eye Fluid and Membranes and Application of the HPPs in the Treatments of Intraocular Pressure (IOP)

Prostaglandins are highly effective ocular hypotensive agents and are ideally suited for the long-term medical management of glaucoma (Woodward, D. F. et al., U.S. Pat. No. 5,688,819). Such prostaglandins include PGA$_1$, PGA$_2$, PGA$_3$, PGB$_1$, PGB$_2$, PGB$_3$, PGD$_1$, PGD$_2$, PGD$_3$, PGE$_1$, PGE$_2$, PGE$_3$, PGF$_{1\alpha}$, PGF$_{1\beta}$, PGF$_{2\alpha}$, PGF$_{2\beta}$, PGF$_{3\alpha}$, PGG$_2$, PGH$_1$, PGH$_2$, PGI$_2$ (prostacyclin), PGI$_3$, PGJ$_2$, PGK$_1$, PGK$_2$, and their alkyl esters were reported to possess ocular hypotensive activity, but generally cause inflammation, as well as surface irritation characterized by conjunctival hyperemia and edema. Certain phenyl and phenoxy mono, tri and tetra nor prostaglandin and their esters disclosed in European Patent Application 0,364,417 are useful in the treatment of glaucoma or ocular hypertension. Buchmann et al. (Buchmann. Et al., U.S. Pat. No. 5,756,818) discloses certain species of cyclopentane heptanoic acid, 2-cycloalkyl, or aryalkyl compounds said to be suitable for lowering intraocular pressure. Woodward et al. (Woodward, D. F. et al., U.S. Pat. No. 5,688,819) disclosed that cyclopentane heptanoic acid, 2-cycloalkyl, or aryalkyl compounds are useful in the treatment of glaucoma or ocular hypertension.

The ability of certain compounds of the present invention to reduce intraocular pressure (IOP) was evaluated in cats with ocular hypertension produced by previously done laser trabeculoplastry. IOP was determined with a pneumatonometer after light corneal anesthesia with dilute proparacaine. Baseline IOP was determined prior to treatment with the test compound aqueous solution. 6 divided doses were administered over a period of 3 days (once every 12 hours). IOP was determined 24 hours after the initial dose and then once every 12 hours. The therapeutically efficient amount is typically between 0.001 and 0.01% in pH 7.2 phosphate buffer (0.1 M). The treatment was carried out in that one drop (about 30 micro liter) of the composition. The results of N,N-diethylaminoethyl 11,15-dihydroxy-9-oxoprost-13-en-1-oate.AcOH (A), N,N-diethylaminoethyl 11,15-dihydroxyl-9-oxoprosta-5,13-dien-1-oate.AcOH (B), N,N-diethylaminoethyl 9,11,15-trihydroxyprosta-5,13-dien-1-oate.AcOH(C), N,N-diethylaminoethyl 9,11-dihydroxy-15-keto-20-ethylprost-5,13-dien-1-oate.AcOH (9,11-dihydroxy-15-keto-20-ethylprostaglandin F$_{2\alpha}$ N,N-diethylaminoethyl ester) (D), N,N-diethylaminoethyl (Z)-7-{(1R,2R,3R,5S)-3,5-dihydroxy-2-[(1E,3R)-3-hydroxy-4-[(α,α,α-trifluoro-m-tolyl)oxy]-1-butenyl]cyclopentyl}-5-heptenoate.AcOH (E), N,N-diethylaminoethyl (Z)-7{(1R,2R,3R,5S)-3,5-dihydroxy-2-[(3R)-3-hydroxy-5-phenylpentyl]cyclopentyl}-5-heptenoate.AcOH (F), and N,N-diethylaminoethyl (Z)-7-{(1R,2R,3R,5S)-3,5-Dihydroxy-2-[(1E,3S)-3-hydroxy-5-phenyl-1-pentenyl]cyclopentyl}-heptenoate.AcOH (G) are shown in Table 2.

TABLE 2

Intraocular pressure reduction by the prodrugs of natural prostaglandin and modified analogs as determined in cats.

| Compound | Baseline | Dose % | Time after administration (hours) | | | | |
|---|---|---|---|---|---|---|---|
| | | | 24 | 36 | 48 | 60 | 72 |
| A | 22.1 ± 0.7 | 0.001 | 15.3 ± 0.4 | 15.1 ± 0.5 | 15.0 ± 0.4 | 15.1 ± 0.5 | 15.4 ± 0.4 |
| B | 22.3 ± 0.6 | 0.001 | 15.7 ± 0.5 | 15.8 ± 0.5 | 15.9 ± 0.4 | 15.7 ± 0.4 | 15.9 ± 0.5 |
| C | 22.5 ± 0.7 | 0.001 | 15.5 ± 0.5 | 15.6 ± 0.6 | 15.7 ± 0.5 | 15.6 ± 0.7 | 15.5 ± 0.6 |
| D | 22.0 ± 0.6 | 0.01 | 16.5 ± 0.6 | 16.7 ± 0.4 | 16.8 ± 0.6 | 17.1 ± 0.5 | 16.8 ± 0.5 |
| E | 22.1 ± 0.4 | 0.001 | 15.1 ± 0.4 | 15.0 ± 0.5 | 15.0 ± 0.4 | 14.9 ± 0.3 | 15.1 ± 0.4 |
| F | 22.5 ± 0.5 | 0.001 | 15.6 ± 0.5 | 15.7 ± 0.4 | 15.6 ± 0.5 | 15.5 ± 0.4 | 15.6 ± 0.6 |
| G | 22.4 ± 0.6 | 0.001 | 15.2 ± 0.6 | 15.4 ± 0.5 | 15.5 ± 0.4 | 15.4 ± 0.6 | 15.4 ± 0.5 |

Recently, unoprostone, travoprost, latanoprost, and bimatoprost are becoming a leading class of glaucoma drugs. These drugs all have side effects due to their very low penetration rates. These side effects included blurred vision, redness, a sensation of a foreign body, discoloration of the iris, itching, burning, stinging, dryness of the eyes, increased tearing, eye pain and other eye-related discomfort.

Irritative effect or ocular discomfort in the cat eye of naturally occurring and modified prostaglandins and their novel prodrugs were evaluated during the first hours after the topical application of the respective test drug. The ocular discomfort was graded on a scale from 0 to 4, 0 indicating complete absence of any signs of discomfort, and 4 indicating maximal irritation as obvious from complete lid closure. The results are shown in Table 3.

TABLE 3

Irritative effect of naturally occurring and modified prostaglandins and their novel prodrugs during the first 2 hours after topical application of the respective test drug.

| Compound | Dose % | Degree of irritative effect |
|---|---|---|
| $PGE_1$ | 0.001 | 4 |
| A | 0.001 | 1 |
| $PGE_2$ | 0.001 | 3.5 |
| B | 0.001 | 1 |
| $PGF_{2\alpha}$ | 0.001 | 3.5 |
| C | 0.001 | 1 |
| Unoprostone | 0.01 | 2.5 |
| D | 0.01 | 1 |
| Travoprost | 0.001 | 2.5 |
| E | 0.001 | 1 |
| latanoprost | 0.001 | 2.5 |
| F | 0.001 | 1 |
| Bimatoprost | 0.001 | 2.5 |
| G | 0.001 | 1 |

B. Transportation of HPPs Through Eye Fluid and Membranes and Application of the HPPs in the Treatments of Conjunctival Hyperemia Conjunctival hyperemia in the rabbit eye of naturally occurring and modified prostaglandins and their novel prodrugs was evaluated during the first 2 hours after topical application of the respective test drug. The conjunctival hyperemia was graded on a scale from 0 to 4, 0 indicating complete absence of any hyperemia, and 4 indicating marked hyperemia with conjunctive chemosis. The results are shown in Table 4.

TABLE 4

Conjunctival hyperemia in the rabbit eye of naturally occurring and modified prostaglandins and their novel prodrugs during the first 2 hours after the topical application of the respective test drug.

| Compound | Dose % | Degree of irritative effect |
|---|---|---|
| $PGE_1$ | 0.001 | 4 |
| A | 0.001 | 1 |
| $PGE_2$ | 0.001 | 4 |
| B | 0.001 | 1 |
| $PGF_{2\alpha}$ | 0.001 | 4 |
| C | 0.001 | 1 |
| Unoprostone | 0.01 | 2.5 |
| D | 0.01 | 1 |
| Travoprost | 0.001 | 2.5 |
| E | 0.001 | 1 |
| Travoprost | 0.001 | 2.5 |
| F | 0.001 | 1 |
| Bimatoprost | 0.001 | 2.5 |
| G | 0.001 | 1 |

The results show that these prodrugs are superior to their parent drugs for the treatment of ocular hypertension and glaucoma. They exhibit excellent intraocular pressure lowering effects, and cause no side effects or very mild side effects. Prostaglandins and related compounds are very lipophilic. When PGs are topically applied to eyes, they do not dissolve in the aqueous humor of the eye. They stay outside of the eye membranes for a long time and thus, may cause pain, itching, or swelling of the eye. Without being bound to a theory, when HPPs of prostaglandins or prostaglandin analogs are topically applied to eyes, the HPPs will dissolve in the aqueous humor of eye immediately. The positive charge on the amino groups of these HPPs will bond to the negative charge on the phosphate head group of membrane of eye. Thus, the local concentration of the outside of the membrane will be very high and will facilitate the passage of these pro-drugs from a region of high concentration to a region of low concentration. When these HPPs enter the membrane, the hydrophilic part will push the HPPs into the cytosol. Due to the short stay outside of the membranes of the eye or skin and thus, the HPPs will not cause burning, pain, itching, or swelling of the eye.

C. Transportation of HPPs Through Human Skin and Application of the HPPs in the Treatments of Sexual Dysfunctions Prostaglandins and related compounds and analogs can also be used for the treatment of male erectile dysfunction (Yeager; J. L., et al. U.S. Pat. No. 6,693,135) and enhancing female sexual arousal (Scott, N. E. U.S. Pat. No. 6,291,528). However, working alone, prostaglandins formulations do not sufficiently permeate the skin to provide drug concentration levels. For example, in one commercially available form (MUSE™, Vivus, Menlo Park Calif.), alprostadil ($PGE_1$) is administered in a pellet deposited in the urethra using an applicator with a hollow stem 3.2 cm in length and 3.5 mm in diameter (Padma-Nathan, H., et al., N. Engl. J. Med., 336: 1-7 (1997) for treatment of impotence. The side effects of this treatment are penile pain and minor urethral trauma. Transurethral delivery of $PGE_1$ or $PGE_2$ is a highly effective means of treating impotence, but there are undesirable side effects that include a sensation of urethral burning or pain and cavernous sinus aching in the genital area. Transurethral delivery of PGs has another problem for removal to terminate delivery of the composition and can result in overdosing as well as the delivery of excess PGs to the vagina of the partner. In one commercially available form, $PGE_1$ is administered by intracavernosal injection. The principal side effect of intracavernosal injection of alprostadil ($PGE_1$) is pain, an incidence of fibrosis and scar formation at the site of injection.

The HPP of the invention can diffuse through human skin in very high rate ($\sim 1$ mg/h/cm$^2$) and can provide almost side-effects-free methods of treating erectile dysfunction or enhancing female sexual arousal. About 0.01 ml of 0.0005% [~0.05 µg (microgram)] N,N-diethylaminoethyl 11,15-dihydroxy-9-oxoprost-13-en-1-oate.AcOH in pH 7.0 phosphate buffer (0.1 M) was applied to genital area of male rats (30 rats) once per day for 5 days. The results showed that 6 fold increase in solicitation and 4 fold increase in copulation in rats that were given the drug compared to those which were not.

When same amount of N,N-diethylaminoethyl 11,15-dihydroxy-9-oxoprost-13-en-1-oate.AcOH in pH 7.0 phosphate buffer (0.1 M) were applied to genital area of both male rats (30 rats) and female rats (30 rates) once per day for 5 days. The results showed that 6 fold increase in solicitation and 6 fold increase in copulation in rats that were given the drug compared to those which were not. The most important thing is that rats that were given the drug did not show any discomfort.

D. Transportation of HPPs Through Skin/Plasma/Membranes and Application of the HPPs in the Treatments of Abnormal Blood Pressure Prostaglandins selected from the group consisting of natural and synthetic analogs of the PGE, PGA, and PGF are useful for reducing systemic blood pressure. 0.02 mg of N,N-diethylaminoethyl 11,15-dihydroxy-9-oxoprosta-5,13-dien-1-oate.AcOH (A) and N,N-diethylaminoethyl 11,16-dihydroxy-9-oxo-16-vinylprosta-5,13-dien-1-oate.AcOH (B) in 0.3 ml of pH 7.0 phosphate buffer (0.1 M) were applied to the back of spontaneously hypertensive rats (after intake of the tungsten-enriched diet. The blood pressure was recorded continuously on a multichannel physiograph. The results are shown in table 5.

TABLE 5

Effect of the prodrugs of prostaglandins on the mean arterial blood pressure in spontaneously hypertensive rats. All values are reported as mean ± SD.

| Compound | Base-line | Time after administration (hours) | | | | |
|---|---|---|---|---|---|---|
| | | 1 | 2 | 3 | 4 | 5 |
| A | 181.4 ± 7.5 | 148.2 ± 7.4 | 143.2 ± 7.6 | 142.2 ± 6.4 | 143.2 ± 7.8 | 145.2 ± 7.0 |
| B | 183.5 ± 8.6 | 155.2 ± 8.2 | 153.2 ± 6.8 | 150.2 ± 7.8 | 153.2 ± 7.0 | 155.2 ± 6.4 |

The mean arterial blood pressure in spontaneously hypertensive rats was significantly reduced after transdermal administration of the prodrugs of prostaglandins and rats that were given the drug did not show any discomfort.

What is claimed is:

1. A compound selected from
   N,N-diethylaminoethyl 11,15-dihydroxy-9-oxoprost-13-en-1-oate.AcOH and
   N,N-diethylaminoethyl 11,16-dihydroxy-9-oxo-16-methylprost-13-en-1-oate.AcOH.

2. A pharmaceutical composition comprising the compound according to claim 1 and a pharmaceutically acceptable carrier selected from the group consisting of sugars, starches, cellulose, cellulose derivatives, tragacanth, malt, gelatin, talc, cocoa butter, suppository waxes, oils, glycols, polyols, esters, agar, buffering agents, alginic acid, water, aqueous solutions, buffered saline, Ringer's solution, ethyl alcohol, phosphate buffer solutions, acetone, sodium citrate, and dicalcium phosphate.

3. The pharmaceutical composition according to claim 2; wherein the pharmaceutically acceptable carrier is polar.

4. The pharmaceutical composition according to claim 2; wherein the pharmaceutically acceptable carrier is selected from ethyl alcohol, acetone, esters, water, and aqueous solutions.

5. A compound selected from:
   N,N-diethylaminoethyl 9,11,15-trihydroxyprost-13-en-1-oate.HA;
   N,N-di ethylaminoethyl 9,11,15-trihydroxy-15-methyl-prosta-5,13-dien-1-oate.HA;
   N,N-diethylaminoethyl 9,11,15-trihydroxy-15-methyl-prosta-4,5,13-trien-1-oate.HA;
   N,N-diethylaminoethyl 9,11-dihydroxy-15-keto-20-ethylprosta-5,13-dien-1-oate.HA; and
   N,N-diethylaminoethyl 11,16-dihydroxy-9-oxo-16-methylprost-13-en-1-oate.HA, wherein HA is acetic acid.

6. A pharmaceutical composition comprising the compound according to claim 5 and a pharmaceutically acceptable carrier selected from the group consisting of sugars, starches, cellulose, cellulose derivatives, tragacanth, malt, gelatin, talc, cocoa butter, suppository waxes, oils, glycols, polyols, esters, agar, buffering agents, alginic acid, water, aqueous solutions, buffered saline, Ringer's solution, ethyl alcohol, phosphate buffer solutions, acetone, sodium citrate, and dicalcium phosphate.

7. The pharmaceutical composition according to claim 6, wherein the pharmaceutically acceptable carrier is polar.

8. The pharmaceutical composition according to claim 6, wherein the pharmaceutically acceptable carrier is selected from ethyl alcohol, acetone, esters, water, and aqueous solutions.

* * * * *